United States Patent
Fukuzawa et al.

(10) Patent No.: US 11,827,924 B2
(45) Date of Patent: *Nov. 28, 2023

(54) PCR REACTION VESSEL, PCR DEVICE, AND PCR METHOD

(71) Applicants: Nippon Sheet Glass Company, Limited, Tokyo (JP); NATIONAL INSTITUTE OF ADVANCED INDUSTRIAL SCIENCE AND TECHNOLOGY, Tokyo (JP); Go!Foton, Inc., Tsukuba Ibaraki (JP)

(72) Inventors: Takashi Fukuzawa, Tokyo (JP); Hidenori Nagai, Osaka (JP); Naofumi Nishizawa, Ibaraki (JP)

(73) Assignee: Go!Foton, Inc., Tsukuba (JP)

( * ) Notice: Subject to any disclaimer, the term of this patent is extended or adjusted under 35 U.S.C. 154(b) by 296 days.

This patent is subject to a terminal disclaimer.

(21) Appl. No.: 17/209,602

(22) Filed: Mar. 23, 2021

(65) Prior Publication Data

US 2021/0207205 A1    Jul. 8, 2021

Related U.S. Application Data

(60) Division of application No. 15/993,814, filed on May 31, 2018, now Pat. No. 10,988,800, which is a continuation of application No. PCT/JP2016/085216, filed on Nov. 28, 2016.

(30) Foreign Application Priority Data

Dec. 1, 2015 (JP) ................................ 2015-235129

(51) Int. Cl.
| | | |
|---|---|---|
| C12P 19/34 | (2006.01) | |
| C12Q 1/6848 | (2018.01) | |
| G01N 37/00 | (2006.01) | |
| C12M 1/00 | (2006.01) | |
| G01N 35/08 | (2006.01) | |
| B01L 3/00 | (2006.01) | |
| B01L 7/00 | (2006.01) | |
| C12Q 1/686 | (2018.01) | |
| G01N 21/64 | (2006.01) | |

(52) U.S. Cl.
CPC .......... *C12Q 1/6848* (2013.01); *B01L 3/502* (2013.01); *B01L 7/52* (2013.01); *C12M 1/00* (2013.01); *C12Q 1/686* (2013.01); *G01N 21/64* (2013.01); *G01N 35/08* (2013.01); *G01N 37/00* (2013.01); *B01L 2200/0689* (2013.01); *B01L 2300/0681* (2013.01); *B01L 2300/0883* (2013.01); *B01L 2300/14* (2013.01); *B01L 2400/0487* (2013.01)

(58) Field of Classification Search
CPC ................. C12Q 1/6848; C12Q 1/686
See application file for complete search history.

(56) References Cited

U.S. PATENT DOCUMENTS

| | | |
|---|---|---|
| 9,731,297 B2 | 8/2017 | Glezer |
| 2005/0202489 A1 | 9/2005 | Cho |
| 2005/0255007 A1 | 11/2005 | Yamada et al. |
| 2006/0013726 A1 | 1/2006 | Munenaka |
| 2009/0325276 A1 | 12/2009 | Battrell et al. |
| 2012/0178091 A1 | 7/2012 | Glezer et al. |
| 2021/0060567 A1 | 3/2021 | Glezer et al. |

FOREIGN PATENT DOCUMENTS

| | | |
|---|---|---|
| CN | 102220225 A | 10/2011 |
| CN | 202898426 U | 4/2013 |
| JP | 2003-279471 A | 10/2003 |
| JP | 2004-309270 A | 11/2004 |
| JP | 2005253466 A | 9/2005 |
| JP | 2005-323519 A | 11/2005 |
| JP | 2006-25661 A | 2/2006 |
| JP | 2009-232700 A | 10/2009 |
| JP | 2009232700 A | 10/2009 |
| JP | 2014-507937 A | 4/2014 |
| JP | 2014507937 A | 4/2014 |
| JP | 2014163713 A | 9/2014 |
| JP | 2014-212705 A | 11/2014 |
| JP | 2015-139379 A | 8/2015 |
| JP | 2016049064 A | 4/2016 |
| WO | 2008018904 A2 | 2/2008 |
| WO | 2008/147382 A8 | 12/2008 |

OTHER PUBLICATIONS

Office Action dated Mar. 29, 2022 from the Indian Intellectual Property Office in IN Application No. 201817023897.
Extended European Search Report dated Sep. 13, 2021 in Application No. 21158865.2.
Communication dated Sep. 1, 2022 from the European Patent Office in Application No. 21158865.2.
Office Action dated Oct. 4, 2022 from the Japanese Patent Office in JP Application No. 2021-006545.
Office Action dated Oct. 11, 2021 in Chinese Application No. 201680069395.8.

(Continued)

*Primary Examiner* — Kenneth R Horlick
(74) *Attorney, Agent, or Firm* — Sughrue Mion, PLLC

(57) ABSTRACT

A PCR reaction vessel includes: a substrate; a channel formed on the substrate; a pair of filters, a first filter and a second filter, provided at respective ends of the channel; a pair of air communication ports, a first air communication port and a second air communication port, that communicate with the channel through the first filter and the second filter; a thermal cycle region formed between the first filter and the second filter in the channel; a branch point formed between the first filter and the second filter in the channel; a branched channel whose one end is connected to the branch point; and a sample introduction port formed at the other end of the branched channel.

18 Claims, 15 Drawing Sheets

(56) References Cited

OTHER PUBLICATIONS

Statement of Opposition from the third party dated Aug. 6, 2021 to the Japanese Patent Office in JP Application No. 2020-103879 (U.S. Pat. No. 6,827,581).
Notification of Reasons for Refusal dated Mar. 29, 2022 from the Japanese Patent Office in Japanese Application No. 2021-006545.
International Preliminary Report on Patentability with a Translation of Written Opinion issued from the International Bureau in counterpart International Application No. PCT/JP2016/085216, dated Jun. 14, 2018.
International Search Report, issued by International Searching Authority in corresponding International Application No. PCT/JP2016/085216, dated Feb. 21, 2017.
Zhang, C. et al., "Micropumps, microvalves, and micromixers within PCR microfluidic chips: Advances and trends," Biotechnology Advances, 2007, pp. 483-514, vol. 25 (32 pages total).
Communication dated May 27, 2019, from the European Patent Office in counterpart European Application No. 16870611.7.
Communication dated Jul. 30, 2019 from the Japanese Patent Office in application No. 2017-553847.
Chiou et al., "A Closed-Cycle Capillary Polymerase Chain Reaction Machine", Analytical Chemistry, vol. 73, No. 9, May 1, 2001, pp. 2018-2021.
Communication dated Jan. 21, 2020 by the European Patent Office in application No. 16 870 611.7.
Office Action dated Mar. 24, 2020 in Japanese Application No. 2017-553847.
Office Action dated Mar. 31, 2020 in Japanese Application No. 2019-212253.
Communication dated Aug. 18, 2020 by the Japanese Patent Office in application No. 2020-103879.
Communication dated Jan. 22, 2019, from the Singapore Patent Office in counterpart application No. 11201804584W.
Office Action dated Mar. 31, 2020 in Japanese Application No. 2019-212254.
Office Action dated Jun. 22, 2020 in European Application No. 16870611.7.
Office Action dated Oct. 27, 2020 in Japanese Application No. 2020-103879.
Office Action dated Dec. 28, 2020 in Chinese Application No. 201680069395.8.
Communication dated May 2, 2020, from the Singapore Patent Office in counterpart application No. 11201804584W.
Japanese Office Action dated Feb. 28, 2023 in Japanese Application No. 2021-006545.

PCR REACTION VESSEL, PCR DEVICE, AND PCR METHOD

CROSS REFERENCE TO RELATED APPLICATIONS

This is a Divisional of application Ser. No. 15/993,814 filed May 31, 2018, now issued as U.S. Pat. No. 10,988,800 on Apr. 27, 2021, claiming priority based on International Application No. PCT/JP2016/085216 filed Nov. 28, 2016, claiming priority based on Japanese Patent Application No. 2015-235129 filed Dec. 1, 2015, the disclosures of which are incorporated herein in their entirety by reference.

BACKGROUND OF THE INVENTION

1. Field of the Invention

The present invention relates to PCR (Polymerase Chain Reaction) reaction vessels used for polymerase chain reactions and to PCR devices and PCR methods in which the PCR reaction vessels are used.

BACKGROUND ART

Genetic testing is widely used for examinations in a wide variety of medical fields, identification of farm products and pathogenic microorganisms safety assessment for food products, and even for examinations for pathogenic viruses and a variety of infectious diseases. In order to detect with high sensitivity a minute amount of gene's DNA, methods of analyzing the resultant obtained by amplifying a portion of DNA are known. Above all, a PCR method is a remarkable technology where a certain portion of a very small amount of DNA collected from an organism or the like is selectively amplified. In a PCR method, a predetermined thermal cycle is applied to a sample in which a biological sample containing DNA and a PCR reagent consisting of primers, enzymes, and the like are mixed so as to cause reactions such as denaturation, annealing, and elongation to be repeated so that a specific portion of DNA is selectively amplified.

It is a common practice to perform a PCR method by putting a predetermined amount of a target sample into a PCR tube or a reaction vessel such as a microplate (microwell) in which a plurality of holes are formed. However, in recent years, it has been put to practical use to perform a PCR method while using a reaction vessel (also referred to as "chip") provided with a micro-channel that is formed on a substrate. In any reaction vessel, the progress of various technologies allow a predetermined thermal cycle to be provided with high speed and high accuracy in the reaction vessel.

Patent document No. 1 discloses a reaction vessel in which a channel for performing PCR is formed. In this reaction vessel, the channel is formed between two overlapping resin substrates, and a sample introduction port for introducing a sample into the channel and a sample discharge port for discharging the sample via through holes formed in the resin substrates are ensured. In a recessed portion on the back surface of a resin substrate, a temperature adjusting unit consisting of, for example, a Peltier element or the like is arranged. A nozzle is arranged at the sample introduction port of the reaction vessel, and the sample can be moved in the channel by feeding and/or suctioning the air through the nozzle.

[Patent document No. 1] Japanese Patent Application Publication No. 2009-232700.

SUMMARY OF THE INVENTION

In a PCR method, it is necessary to prevent contamination into the system from the outside during the processing of a sample. If a contamination includes biological pieces or the like other than those of an object to be processed, there is a possibility of amplifying DNA contained in the biological pieces other than those of the object to be processed. In this case, the analysis that follows cannot be accurately performed using the sample to be processed. Therefore, after introducing the sample into the reaction vessel, it is necessary to take measures in order to prevent contamination.

However, in the invention disclosed in Patent document No. 1, for example, if biological pieces other than those of the object to be processed are attached to the nozzle or a pump that sends the air to the nozzle, the biological pieces other than those of the object to be processed may enter the reaction vessel through the sample introduction port, and contamination may thus occur. Also, it is not realistic from the cost and environmental aspects to discard nozzles, tip parts of pumps, attachments, and the like every single time a PCR process is performed.

In this background, a purpose of the present invention is to provide a PCR reaction vessel capable of suitably preventing contamination and a PCR device and a PCR method in which the PCR reaction vessel is used.

A PCR reaction vessel according to one embodiment of the present invention includes: a substrate; a channel formed on the substrate; a pair of filters provided at respective ends of the channel; a pair of air communication ports that communicate with the channel through the respective filters; a thermal cycle region formed between the pair of filters in the channel; a branch point formed between the pair of filters in the channel; a branched channel whose one end is connected to the branch point; and a sample introduction port formed at the other end of the branched channel.

Another embodiment of the present invention also relates to a PCR reaction vessel. This PCR reaction vessel includes: a substrate; a channel formed on the substrate; a pair of filters provided at respective ends of the channel; a pair of air communication ports that communicate with the channel through the respective filters; a thermal cycle region formed between the pair of filters in the channel; a first branch point formed between the pair of filters in the channel; a first branched channel whose one end is connected to the first branch point; a first sample introduction port formed at the other end of the first branched channel; a second branch point formed between the pair of filters in the channel; a second branched channel whose one end is connected to the second branch point; and a second sample introduction port formed at the other end of the second branched channel.

The PCR reaction vessel may further include a buffer channel region formed between the first branch point and the second branch point in the channel.

The buffer channel region may be set to have a predetermined volume according to the amount of a sample on which a PCR process is intended to be performed.

The thermal cycle region may include a serpentine channel. The thermal cycle region may be provided with a pair of reaction regions each including a serpentine channel and with a connection region connecting the pair of reaction regions.

A sealing film for sealing the air communication ports and the sample introduction ports may be further provided.

The sealing film may be formed such that the sealing film can be perforated by a needle.

Another embodiment of the present invention relates to a PCR device. This device may includes: the above-described PCR reaction vessel; a temperature adjustment unit for adjusting the temperature of the thermal cycle region; and a pump system that controls the pressure inside the channel via the air communication ports in order to move the sample inside the thermal cycle region.

The pump system may be provided with an air pump of a type that allows the pressure on a primary side and the pressure on a secondary side to be equal to each other when stopped.

The air pump may be provided with a nozzle with a hollow needle provided at the tip of the nozzle.

The PCR device may further include a fluorescence detector for detecting fluorescence generated from the sample inside the channel.

The PCR device may further include a control unit for controlling the pump system based on a value detected by the fluorescence detector.

Still another embodiment of the present invention relates to a PCR method. This method includes: preparing a PCR reaction vessel including: a substrate; a channel formed on the substrate; a pair of filters provided at respective ends of the channel; a pair of air communication ports that communicate with the channel through the respective filters; a thermal cycle region formed between the pair of filters in the channel; a branch point formed between the pair of filters in the channel; a branched channel whose one end is connected to the branch point; and a sample introduction port formed at the other end of the branched channel; introducing a sample into the PCR reaction vessel via the sample introduction port; setting the PCR reaction vessel in a PCR device provided with a pump; connecting a nozzle of the pump to the air communication ports; and moving a sample in the thermal cycle region by controlling the pressure inside the channel by the pump.

A sample not subjected to PCR may stay in the branched channel in the moving of a sample.

Still another embodiment of the present invention also relates to a PCR method. This PCR method includes: preparing a PCR reaction vessel including: a substrate; a channel formed on the substrate; a pair of filters provided at respective ends of the channel; a pair of air communication ports that communicate with the channel through the respective filters; a thermal cycle region formed between the pair of filters in the channel; a first branch point formed between the pair of filters in the channel; a first branched channel whose one end is connected to the first branch point; a first sample introduction port formed at the other end of the first branched channel; a second branch point formed between the pair of filters in the channel; a second branched channel whose one end is connected to the second branch point; and a second sample introduction port formed at the other end of the second branched channel; introducing a sample into the PCR reaction vessel via the first sample introduction port and the second sample introduction port; setting the PCR reaction vessel in a PCR device provided with a pump; connecting a nozzle of the pump to the air communication ports; and moving a sample in the thermal cycle region by controlling the pressure inside the channel by the pump.

The PCR reaction vessel may further include a buffer channel region formed between the first branch point and the second branch point in the channel, and the above-described PCR method may further includes: dispensing the sample using the buffer channel region.

A sample not subjected to PCR may stay in the first branched channel and the second branched channel in the moving of a sample.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE INVENTION

Figure 1A:
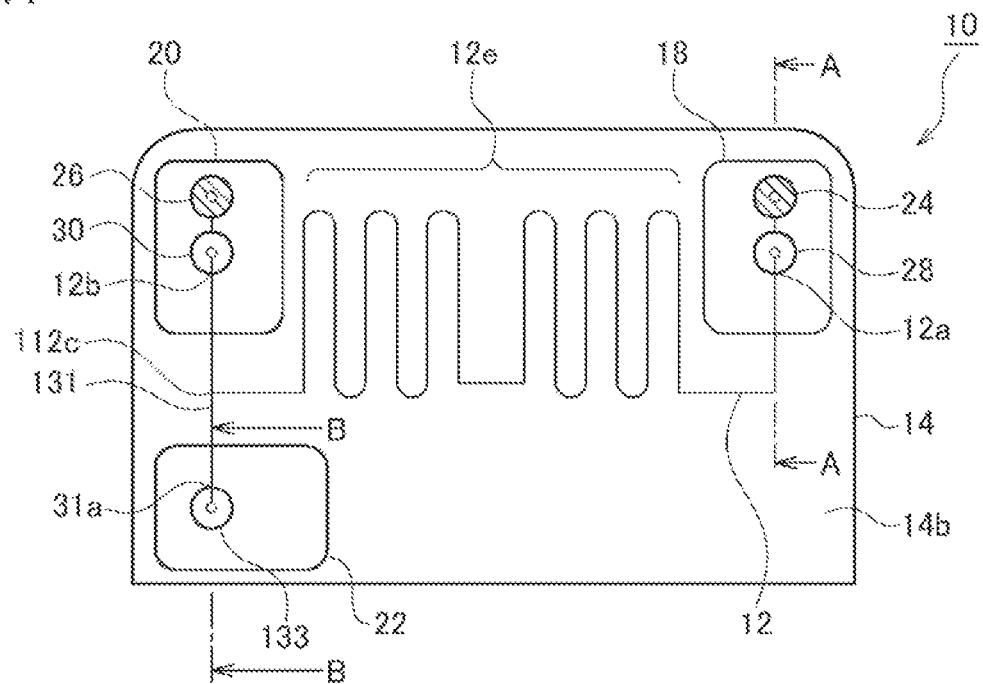
FIGS. 1A and 1B are diagrams for explaining a PCR reaction vessel according to a first embodiment of the present invention.

An explanation will be given in the following regarding a PCR reaction vessel and a PCR device according to an embodiment of the present invention. The same or equivalent constituting elements, members, and processes illustrated in each drawing shall be denoted by the same reference numerals, and duplicative explanations will be omitted appropriately. Reference herein to details of the illustrated embodiments is not intended to limit the scope of the claims. It should be understood that not all of the features and the combination thereof discussed are essential to the invention.

First Embodiment

Figure 1B:
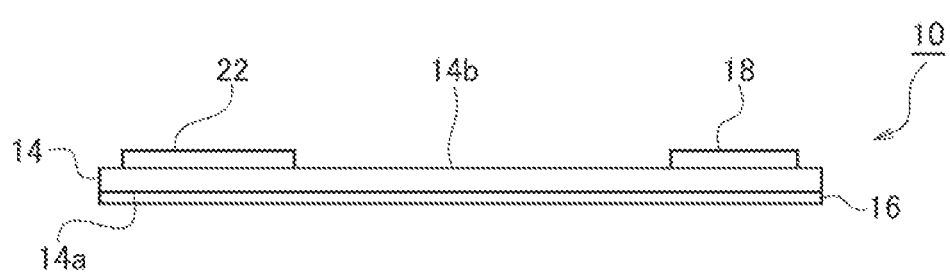
Figure 2:
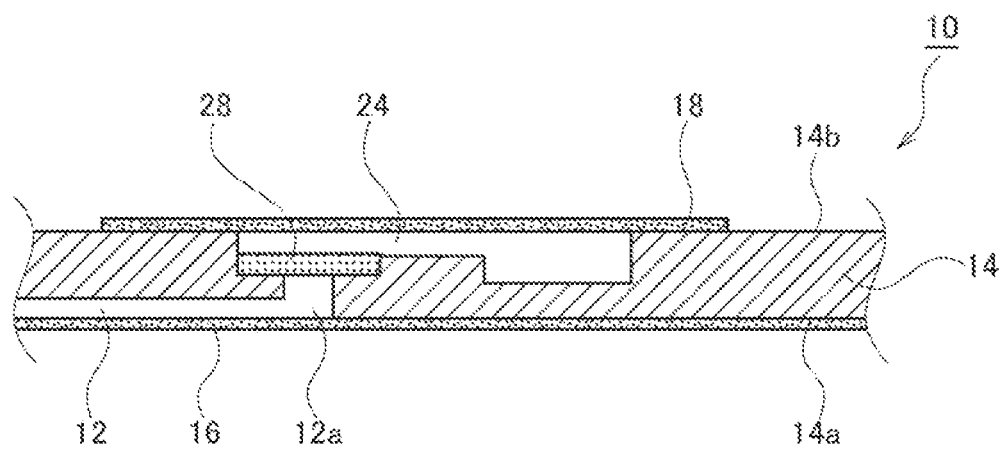
FIG. 2 is a cross-sectional view of the PCR reaction vessel shown in FIG. 1A that is sectioned along line A-A.
Figure 3:
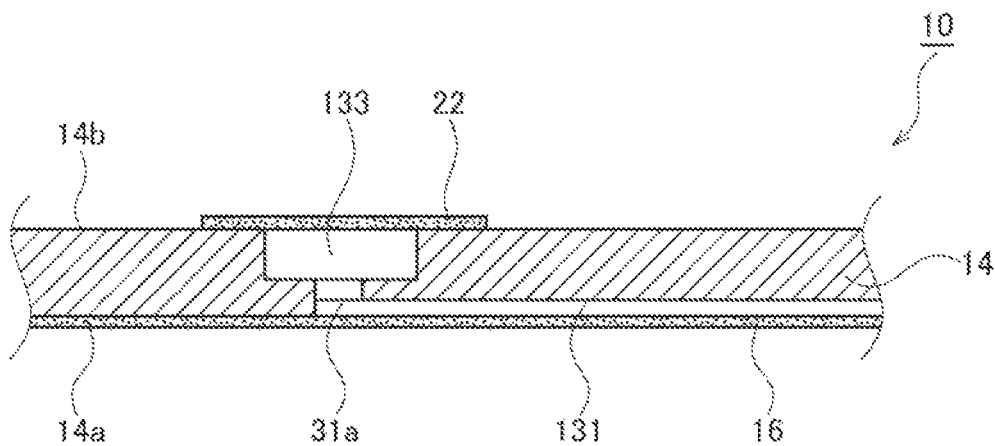
FIG. 3 is a cross-sectional view of the PCR reaction vessel shown in FIG. 1A that is sectioned along line B-B.
Figure 4:
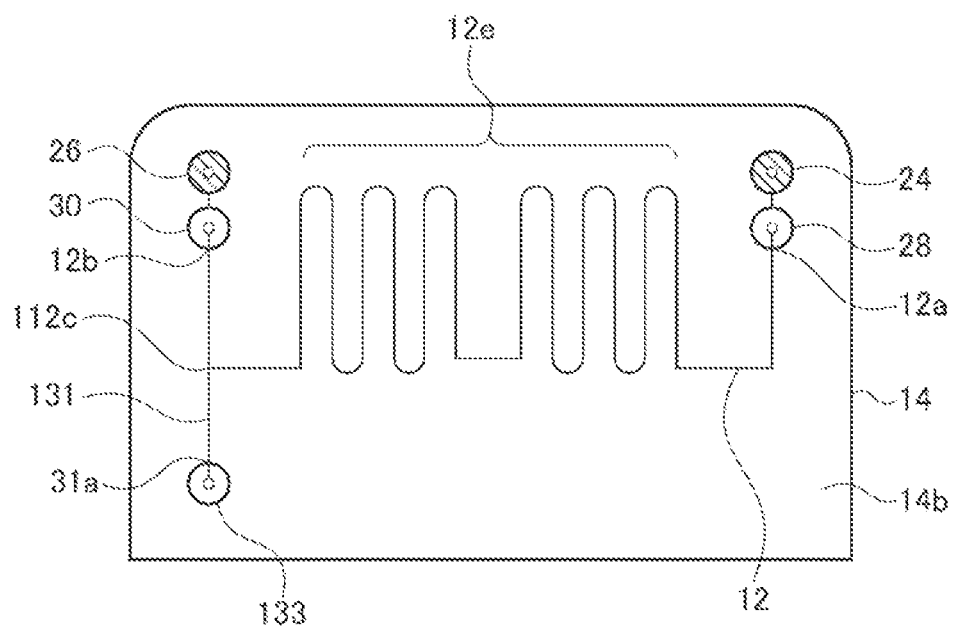
FIG. 4 is a plan view of a substrate provided in the PCR reaction vessel according to the first embodiment.
Figure 5:
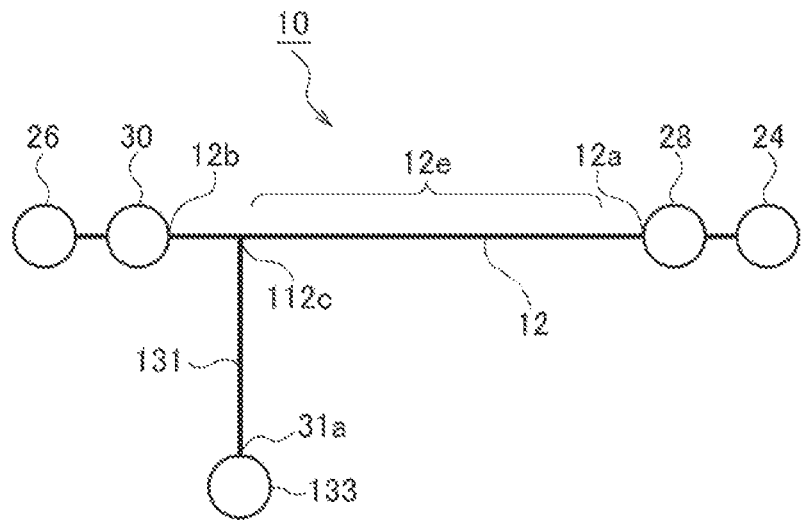
FIG. 5 is a conceptual diagram for explaining the configuration of the PCR reaction vessel according to the first embodiment.

FIGS. 1A and 1B are diagrams for explaining a PCR reaction vessel 10 according to a first embodiment of the present invention. FIG. 1A is a plan view of the PCR reaction vessel 10, and FIG. 1B is a front view of the PCR reaction vessel 10. FIG. 2 is a cross-sectional view of the PCR reaction vessel 10 shown in FIG. 1A that is sectioned along line A-A. FIG. 3 is a cross-sectional view of the PCR reaction vessel 10 shown in FIG. 1A that is sectioned along line B-B. FIG. 4 is a plan view of a substrate 14 provided in the PCR reaction vessel 10. FIG. 5 is a conceptual diagram for explaining the configuration of the PCR reaction vessel 10.

The PCR reaction vessel 10 comprises a resinous substrate 14 having a groove-like channel 12 formed on a lower surface 14a thereof, a channel sealing film 16, which is attached on the lower surface 14a of the substrate 14, for sealing the channel 12, and three sealing films (a first sealing film 18, a second sealing film 20, and a third sealing film 22) attached on an upper surface 14b of the substrate 14.

The substrate 14 is preferably formed of a material that has good thermal conductivity, is stable under temperature changes, and is resistant to a sample solution that is used. Further, the substrate 14 is preferably formed of a material that has good moldability, a good transparency and barrier property, and a low self-fluorescence property. As such a material, an inorganic material such as glass, silicon, or the like, a resin such as acrylic, polyester, silicone, or the like, and particularly cycloolefin are preferred. An example of the dimensions of the substrate 14 includes a long side of 70 mm, a short side of 42 mm, and a thickness of 3 mm. An example of the dimensions of the channel 12 formed on the lower surface 14a of the substrate 14 includes a width of 0.5 mm and a depth of 0.5 mm.

As described above, the groove-like channel 12 is formed on the lower surface 14a of the substrate 14, and this channel 12 is sealed by the channel sealing film 16 (see FIG. 2). A first air communication port 24 is formed at the position of one end 12a of the channel 12 in the substrate 14. A second air communication port 26 is formed at the position of the other end 12b of the channel 12 in the substrate 14. The pair, the first air communication port 24 and the second air communication port 26, is formed so as to be exposed on the upper surface 14b of the substrate 14. Such a substrate can be produced by injection molding or cutting work with an NC processing machine or the like.

A first filter 28 is provided between the first air communication port 24 and one end 12a of the channel 12 in the substrate 14 (see FIG. 2). A second filter 30 is provided between the second air communication port 26 and the other end 12b of the channel 12 in the substrate 14. The pair, the first filter 28 and the second filter 30, provided at respective ends of the channel 12, has good low impurity characteristics and also allows only air to pass therethrough so as to prevent contamination such that the quality of DNA amplified by PCR does not deteriorate. As a filter material, polyethylene, PTFE, and the like are suitable, and the filter material may be porous or hydrophobic. Regarding the dimensions of the first filter 28 and the second filter 30, the first filter 28 and the second filter 30 are formed so as to fit without any gap in a filter installation space formed in the substrate 14.

At a branch point 112c located between the first filter 28 and the second filter 30, a branched channel 131 branching from the channel 12 is formed in the substrate 14. A sample introduction port 133 is formed at the position of a terminal end 31a of the branched channel 131 in the substrate 14 (see FIG. 3). The sample introduction port 133 is formed so as to be exposed on the upper surface 14b of the substrate 14.

A section of the channel 12 that is located between the first filter 28 and the branch point 112c forms a thermal cycle region 12e intended for a high temperature region and a medium temperature region in order to apply a thermal cycle to the sample. The thermal cycle region 12e of the channel 12 includes a serpentine channel. This is for efficiently providing the amount of heat provided from the PCR device during a PCR step to a sample and for allowing the volume of a sample that can be subjected to PCR to be a certain amount or more. In the first embodiment, the branch point 112c is provided between the thermal cycle region 12e and the second filter 30. However, since the branch point 112c is for introducing a sample subjected to PCR through the branched channel 131 and the sample introduction port 133, which are connected to the branch point 112c, there is no functional problem as long as the branch point 112c is formed between the first filter 28 and the second filter 30. Since the PCR reaction vessel 10 is intended to be installed in the PCR device, to provide a thermal cycle to a sample, and to measure optical properties such as fluorescence emitted from the sample, the arrangement of each element including the channels and branch point needs to be arbitrarily selected also in consideration of, e.g., the arrangement of a temperature adjustment unit and a probe for fluorescence detection, which are described later. In the first embodiment, the branch point 112c is arranged on the side closer to the second filter 30, and the thermal cycle region is provided between the branch point 112c and the first filter 28. Therefore, the distance on the channel between the branch point 112c and the first filter 28 can be kept to be relatively large, and a space for efficiently arranging the temperature adjustment unit is formed, when installed in the thermal cycle region and also in the PCR device. On the contrary, when the branch point 112c is arranged on the side closer to the first filter 28, it can be considered to be more reasonable to form the thermal cycle region 12e between the branch point 112c and the second filter 30.

In the PCR reaction vessel 10 according to the first embodiment, most of the channel 12 is formed in the shape of a groove exposed on the lower surface 14a of the substrate 14. This is for allowing for easier molding by injection molding using a metal mold or the like. In order to make use of this groove as a channel, the channel sealing film 16 is attached on the lower surface 14a of the substrate 14. The channel sealing film 16 may be sticky on one of the main surfaces thereof or may have a functional layer that exhibits stickiness or adhesiveness by pressing that is formed on one of the main surfaces. Thus, the channel sealing film 16 has a function of being easily able to become integral with the lower surface 14a of the substrate 14 while being in close contact with the lower surface 14a. The channel sealing film 16 is desirably formed of a material, including an adhesive, that has a low self-fluorescence property. In this respect, a transparent film made of a resin such as a cycloolefin polymer, polyester, polypropylene, polyethylene or acrylic is suitable but is not limited thereto. Further, the channel sealing film 16 may be formed of a plate-like glass or resin. Since rigidity can be expected in this case, the channel sealing film 16 is useful for preventing warpage and deformation of the PCR reaction vessel 10.

Further, in the PCR reaction vessel 10 according to the first embodiment, the first air communication port 24, the second air communication port 26, the first filter 28, the second filter 30, and the sample introduction port 133 are exposed on the upper surface 14b of the substrate 14. Therefore, in order to seal the first air communication port 24 and the first filter 28, the first sealing film 18 is attached to the upper surface 14b of the substrate 14. Also, in order to seal the second air communication port 26 and the second filter 30, the second sealing film 20 is attached to the upper surface 14b of the substrate 14. Further, in order to seal the sample introduction port 133, the third sealing film 22 is attached to the upper surface 14b of the substrate 14.

The first sealing film 18 that is used has a size that is capable of sealing the first air communication port 24 and the first filter 28 at the same time, and the second sealing film 20 that is used has a size that is capable of sealing the second air communication port 26 and the second filter 30 at the same time. A pressure-type pump (described later) is connected to the first air communication port 24 and the second air communication port 26 by perforating the first air communication port 24 and the second air communication port 26 by a hollow needle (syringe needle with a sharp tip) provided at the tip of the pump. Therefore, the first sealing film 18 and the second sealing film 20 are preferably films made of a material that is easily perforated by the needle and/or have a thickness that is easily perforated by the needle. In the first embodiment, sealing films are described that each has a size that allows for the sealing of an air communication port and a filter that are concerned at the same time. However, these air communication port and filter may be sealed separately. Alternatively, a sealing film may be used that can seal the first air communication port 24, the first filter 28, the second air communication port 26, and the second filter 30 all at once (by a single sheet).

As the third sealing film 22, a sealing film having a size that allows for the sealing of the sample introduction port 133 is used. Introduction of a sample into the channel 12 through the sample introduction port 133 is performed by once peeling the third sealing film 22 from the substrate 14, and, after the introduction of a predetermined amount of sample, the third sealing film 22 is put back being attached to the upper surface 14b of the substrate 14 again. Therefore, as the third sealing film 22, a film is desired that is sticky enough to hold up through several cycles of attaching and peeling. Alternatively, as the third sealing film 22, a new film may be attached after the introduction of a sample. In this case, the importance of the property related to attaching and peeling can be lessened.

Also, at the time of the introduction of a sample, it is necessary to once peel off either the first sealing film 18 or the second sealing film 20 in the same way as in the third sealing film 22. This is because the sample does not enter the channel if an air outlet is not created. Therefore, the first sealing film 18 and the second sealing film 20 are desirably films that are sticky enough to hold up through several cycles of attaching and peeling. Alternatively, a new film may be attached after the introduction of a sample.

In the same way as in the channel sealing film 16, the first sealing film 18, the second sealing film 20, and the third sealing film 22 may have an adhesive layer or a functional layer exhibiting stickiness or adhesiveness by pressing that is formed on one of the main surfaces thereof. The first sealing film 18, the second sealing film 20, and the third sealing film 22 are desirably formed of a material, including an adhesive, that has a low self-fluorescence property. In this respect, a transparent film made of a resin such as cycloolefin, polyester, polypropylene, polyethylene or acrylic is suitable but is not limited thereto. As described above, the property such as stickiness or the like desirably do not degrade to such an extent that the use is affected even after attaching and peeling of multiple times. However, in a case where a new film is attached after the peeling and the introduction of a sample or the like, the importance of this property related to the attaching and peeling can be lessened.

An explanation will be given next regarding a method of using the PCR reaction vessel 10 configured as described above. First, a sample to be amplified through a thermal cycle is prepared. The sample includes those obtained by adding a plurality of types of primers, a thermostable enzyme and four types of deoxyribonucleoside triphosphates (dATP, dCTP, dGTP, dTTP) as PCR reagents to a mixture containing two or more types of DNA. Next, the first sealing film 18 and the third sealing film 22 are peeled off from the substrate 14 such that the first air communication port 24 and the sample introduction port 133 are open. In the case where the first sealing film 18 is of a size that is capable of sealing the first air communication port 24 and the first filter 28 at the same time, the first sealing film 18 may be completely peeled from the substrate 14 such that the first air communication port 24 and the first filter 28 are open to the atmospheric air. However, opening only the first air communication port 24 without completely peeling the first sealing film 18 from the substrate 14 is effective in the prevention of contamination since the first filter 28 is not exposed to the atmospheric air. Also, in the case of using a sealing film capable of separately sealing the first air communication port 24 and the first filter 28, the first filter 28 is not exposed to the atmospheric air in the same manner, and the film is thus effective in the prevention of contamination.

Figure 6:
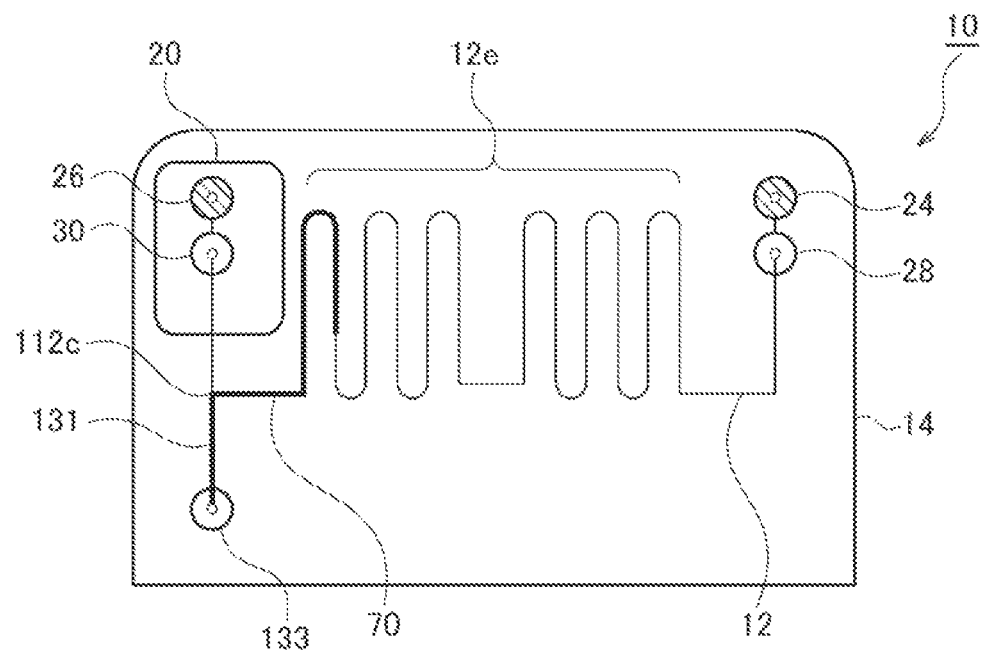
FIG. 6 is a diagram schematically showing a condition where a sample is introduced into the PCR reaction vessel in the first embodiment.

The sample is then introduced to the sample introduction port 133 by a dropper, a syringe, or the like. FIG. 6 schematically shows a condition where a sample 70 is introduced into the PCR reaction vessel 10. In FIG. 6, in order to emphasize the position of the sample 70, the sample 70 is shown by a solid line that is thicker than that for the channel 12. It should be noted that the solid line does not indicate a state where the sample 70 overflows outside the channel.

As shown in FIG. 6, the sample 70 introduced to the sample introduction port 133 fills the channel by being pushed in by a dropper, a syringe, or the like, or by a capillary phenomenon. The sample 70 is packed in the direction of the thermal cycle region 12e (in the direction of the first air communication port 24) beyond the branch point 112c in the channel 12. However, the sample 70 is not packed in the direction of the second air communication port 26 beyond the branch point 112c. This is because the second air communication port 26 is sealed such that there is no outlet for the air to escape.

Figure 7:
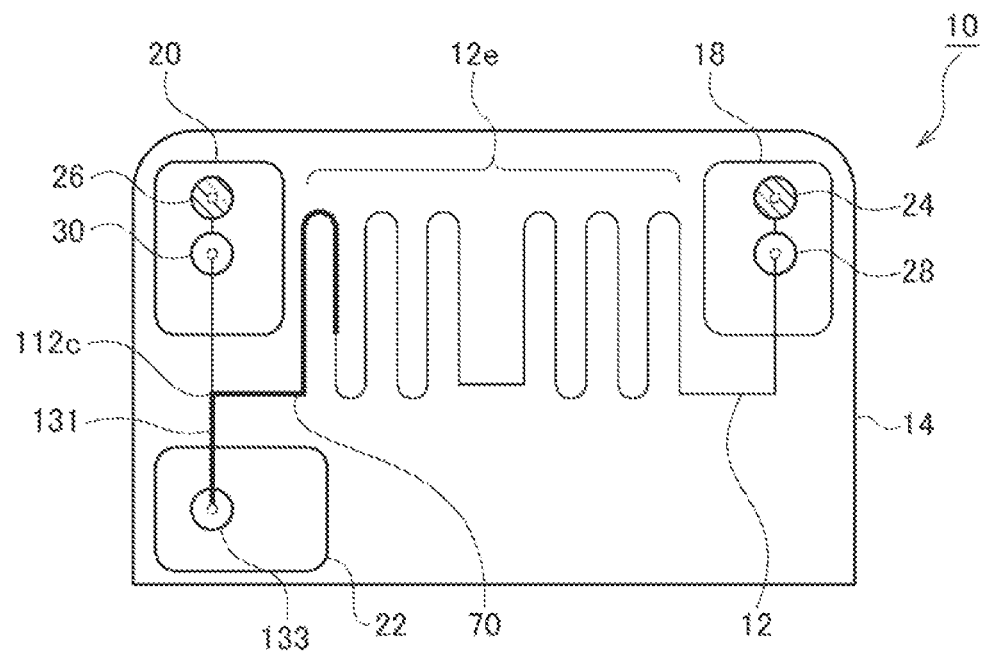
FIG. 7 is a diagram showing a state where a third sealing film is reattached to the substrate in the first embodiment.

Next, as shown in FIG. 7, the first sealing film 18 and the third sealing film 22 are attached to the substrate 14 again so as to seal the first air communication port 24 and the sample introduction port 133. As described above, a new first sealing film 18 and a new third sealing film 22 may be attached. This completes the introduction of the sample 70 into the PCR reaction vessel 10.

Figure 8:
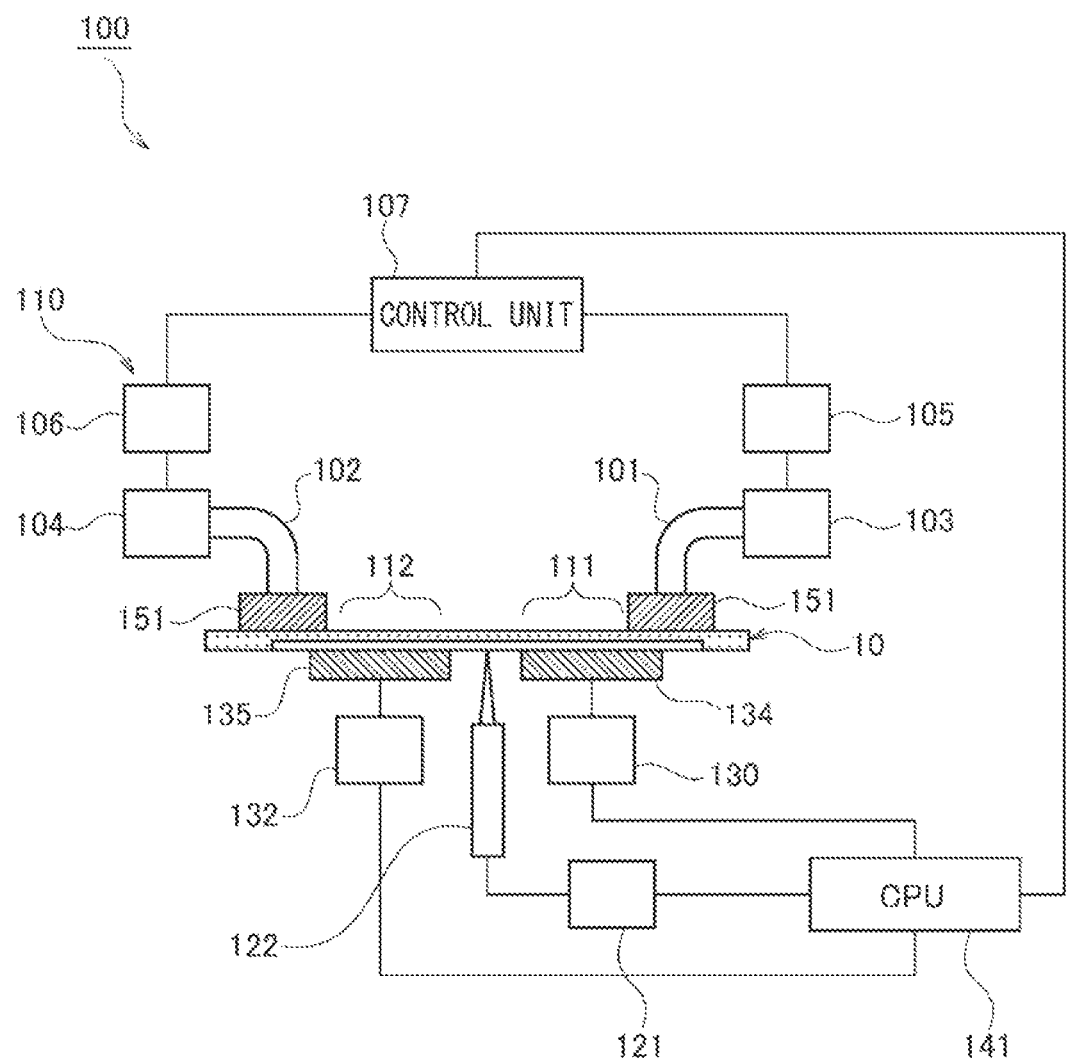
FIG. 8 is a diagram for explaining a PCR device in which the PCR reaction vessel according to the first embodiment is used.
Figure 9:
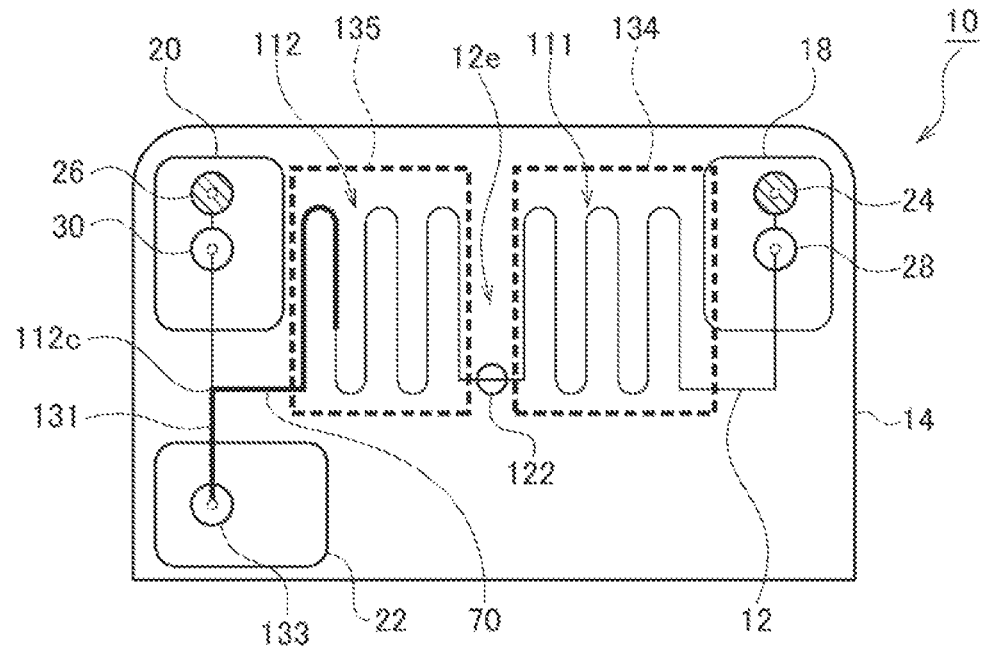
FIG. 9 is a diagram for explaining a state where the PCR reaction vessel is set at a predetermined position of the PCR device in the first embodiment.

FIG. 8 is a diagram for explaining a PCR device 100 in which the PCR reaction vessel 10 is used. FIG. 9 is a diagram for explaining a state where the PCR reaction vessel 10 is set at a predetermined position of the PCR device 100.

The PCR device 100 is provided with a fluorescence detection optical probe 122, a first heater 134, and a second heater 135. As shown in FIG. 9, in the PCR reaction vessel 10, two reaction regions of the thermal cycle region 12e of the channel 12 are arranged on the first heater 134 and the second heater 135, respectively, and the fluorescence detection optical probe 122 is installed in the PCR device 100 so as to be located in a connection region between the two reaction regions.

The PCR device 100 is further provided with a pump system 110 for causing the sample 70 to reciprocate in the thermal cycle region 12e. This pump system 110 is provided with a first nozzle 101, a second nozzle 102, a first pump 103, a second pump 104, a first pump driver 105, a second pump driver 106, and a control unit 107. The first nozzle 101 of the pump system 110 is connected to the first air communication port 24 of the PCR reaction vessel 10, and the second nozzle 102 of the pump system 110 is connected to the second air communication port 26 of the PCR reaction vessel 10. A specific method for connecting the nozzles to the respective air communication ports will be described later. The pump system 110 moves the sample in the thermal cycle region 12e by controlling the pressure inside the channel 12 via the first air communication port 24 and the second air communication port 26.

In the PCR device 100 according to the first embodiment, the first heater 134 and the second heater 135 are set to different temperatures. Each heater provides the amount of heat to individually control the temperatures of the two reaction regions in the thermal cycle region 12e and has an area that covers the area of each of the reaction regions. Also, each heater may be a means or a structure such as resistive heating or a Peltier element. For example, the first heater 134 is controlled by the first heater driver 130 so as to maintain the temperature of the reaction region on the right side of the figure page in the thermal cycle region 12e of the channel 12 to be 94° C. constantly. Also, the second heater 135 is controlled by the second heater driver 132 so as to maintain the temperature of the reaction region on the left side of the figure page to be 60° C. constantly. The temperature of each reaction region may be measured by a temperature sensor (not shown) such as a thermocouple, and the output to each heater may be controlled by each driver based on an electric signal therefrom. In this manner, the first heater 134, the second heater 135, the first heater driver 130, the second heater driver 132, and the temperature sensor may constitute a temperature adjustment unit for adjusting the temperature of the thermal cycle region 12e and may include other elements that improve the controllability of the temperature. In the following, the reaction region at the atmospheric temperature of 94° C. in the channel 12 is referred to as "high temperature part 111", and the reaction region at the atmospheric temperature of 60° C. in the channel 12 is referred to as "medium temperature part 112".

Further, in the present embodiment, a detailed explanation will be given regarding a PCR device that is provided with a PCR reaction vessel provided with a thermal cycle region where temperature ranges of two levels are set as two reaction regions and that is provided with a temperature control unit. However, the PCR device may be provided with a PCR reaction vessel provided with a thermal cycle region where temperature ranges of three or more levels can be set and that is provided with a temperature control unit. In this case, (although not shown), for example, the PCR device may be provided with a PCR reaction vessel provided with reaction regions in which a low temperature part, a medium temperature part, and a high temperature part are arranged from the left side of the figure page and with a temperature control unit. In such a case, for example, the low temperature part, the medium temperature part, and the high temperature part are controlled to maintain 50 to 70° C., at 72° C., and 94° C., respectively.

The pump system 110 is arranged to cause the sample 70 to reciprocate within the thermal cycle region 12e of the channel 12, as described above. By alternately operating the first pump 103 and the second pump 104 through the first pump driver 105 and the second pump driver 106 under a certain condition by the control unit 107, the sample 70 can be reciprocated between the high temperature part 111 and the medium temperature part 112 of the channel 12, and a thermal cycle can be applied to the sample 70 under a certain condition. In the PCR device 100 according to the first embodiment, the first pump 103 and the second pump 104 are air pumps or blower pumps of a type where, when both the first pump 103 and the second pump 104 are stopped, the atmospheric pressures on a primary side and a secondary side instantaneously become equal to each other, and when both first pump 103 and the second pump 104 are being stopped, the atmospheric pressure on the primary side and the atmospheric pressure on the secondary side are equal to each other. If this type of pump is not used, that is, if a pump is used that maintains the immediately preceding pressure even when stopped, there is a possibility that a phenomenon occurs where the sample continues to move slightly even when the pump is stopped such that the sample does not stop in a predetermined reaction region and the temperature of the sample cannot be appropriately controlled. On the other hand, in the PCR device 100 according to the first embodiment, external air and the channel of the PCR reaction vessel communicate with each other in terms of the atmospheric pressure when stopped (when opened), having equal atmospheric pressure; however, since a filter is provided between the air communication port and the channel, contamination into the channel can be prevented.

The sample 70 can undergo PCR by the above-described thermal cycle, and the fluorescence from the sample 70 in the channel can be detected, and the value thereof can be used as an index serving as information for determining the progress of the PCR or the termination of the reaction. As the fluorescence detection optical probe 122 and the driver 121, optical fiber-type fluorescence detector FLE-510 (manufactured by Nippon Sheet Glass Co., Ltd.) can be used, which is a very compact optical system that allows for rapid measurement and the detection of fluorescence regardless of a light and/or dark atmosphere. This optical fiber type fluorescence detector can be also arranged easily in a narrow space between the two reaction regions in the thermal cycle region. This optical fiber type fluorescence detector allows the wavelength characteristic of the excitation light/fluorescence to be tuned such that the wavelength characteristic is suitable for the fluorescence characteristic of the sample 70 and thus allows an optimum optical and detection system for a sample having various characteristics to be provided. Further, fluorescence detection optical probes 122 and drivers 121 may be provided that are installed at a plurality of sites throughout the inside of the thermal cycle region 12e. For example, the fluorescence detection optical probes 122 and drivers 121 may be installed to detect the fluorescence from the sample 70 in the channel located in the high temperature part 111 or the medium temperature part 112. In addition to the function of acquiring information for determining the progress or the termination of the PCR, the fluorescence detection optical probes 122 and drivers 121 can also cause to a function as position sensors for detecting, without fail, whether or not the sample 70 is in the high temperature part 111 or the medium temperature part 112.

In the PCR device 100 configured as described above, the control unit 107 of the pump system 110, the driver 121 of the fluorescence detection optical probe 122, the first heater driver 130, and the second heater driver 132 are controlled to operate optimally by a CPU 141. Also, as described above, in the case where a reaction region in which temperatures of three levels are set, a third heater driver (not shown) is also controlled by the CPU in addition to the above.

Figure 10:
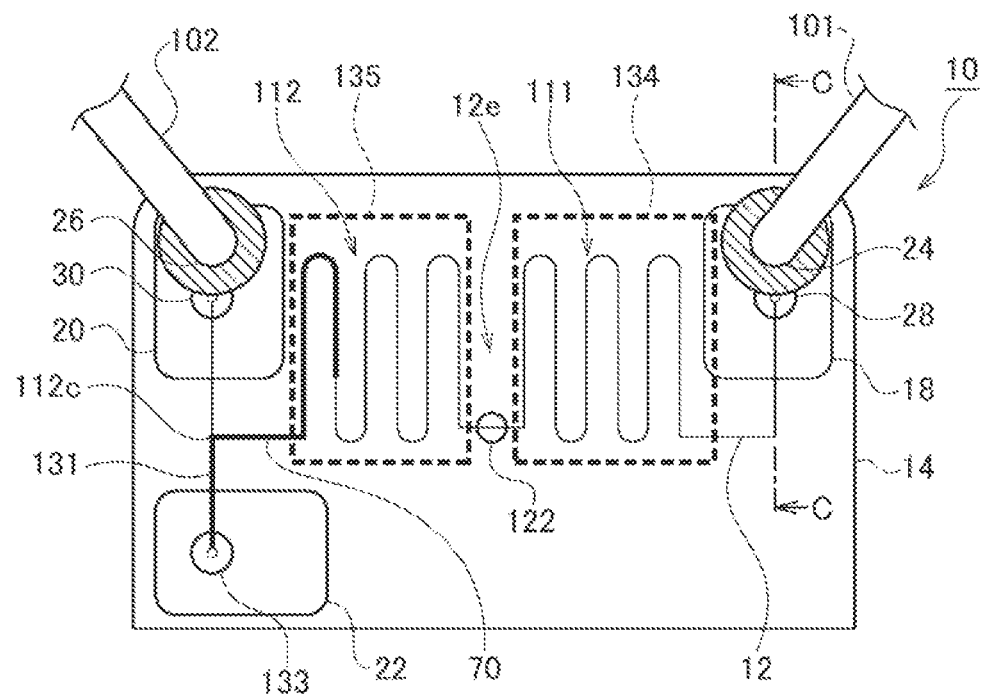
FIG. 10 is a diagram showing a condition where a nozzle of a pump system and an air communication port of the PCR reaction vessel are connected in the first embodiment.
Figure 11:
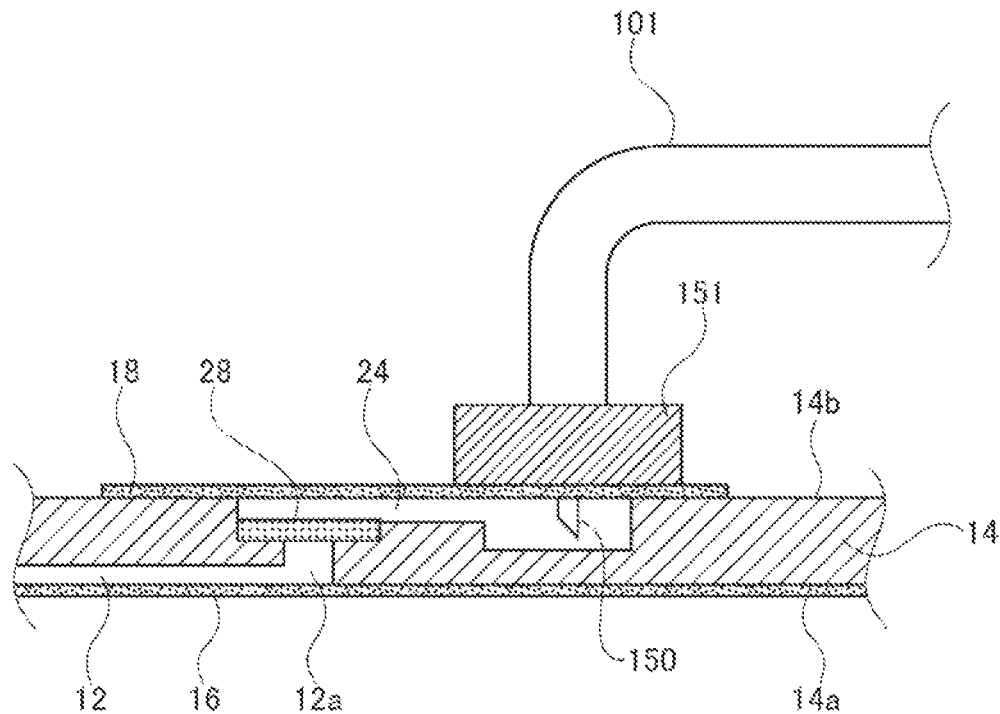
FIG. 11 is a cross-sectional view of the PCR reaction vessel shown in FIG. 10 that is sectioned along line C-C.

FIG. 10 is a diagram showing a condition where a nozzle of a pump system and an air communication port of the PCR reaction vessel are connected. FIG. 11 is a cross-sectional view of the PCR reaction vessel 10 shown in FIG. 10 that is sectioned along line C-C. As described above, the first nozzle 101 is connected to the first air communication port 24, and the second nozzle 102 is connected to the second air communication port 26.

As shown in FIG. 11, a hollow needle 150 is provided at the tip of the first nozzle 101. By perforating the first sealing film 18 with this needle 150, the first nozzle 101 is connected to the first air communication port 24. The same applies to the connection between the second nozzle 102 and the second air communication port 26.

The needle 150 is provided with a packing material 151 made of a soft resin that comes into close contact with the surface of a sealing film in order to secure airtightness around the connection. Immediately after the PCR reaction vessel 10 is set in the PCR device 100, the pump system 110 is not in operation and is open to the atmospheric air, and the pressure inside the channel is thus in a state where the pressure is equal to the atmospheric pressure.

Figure 12:
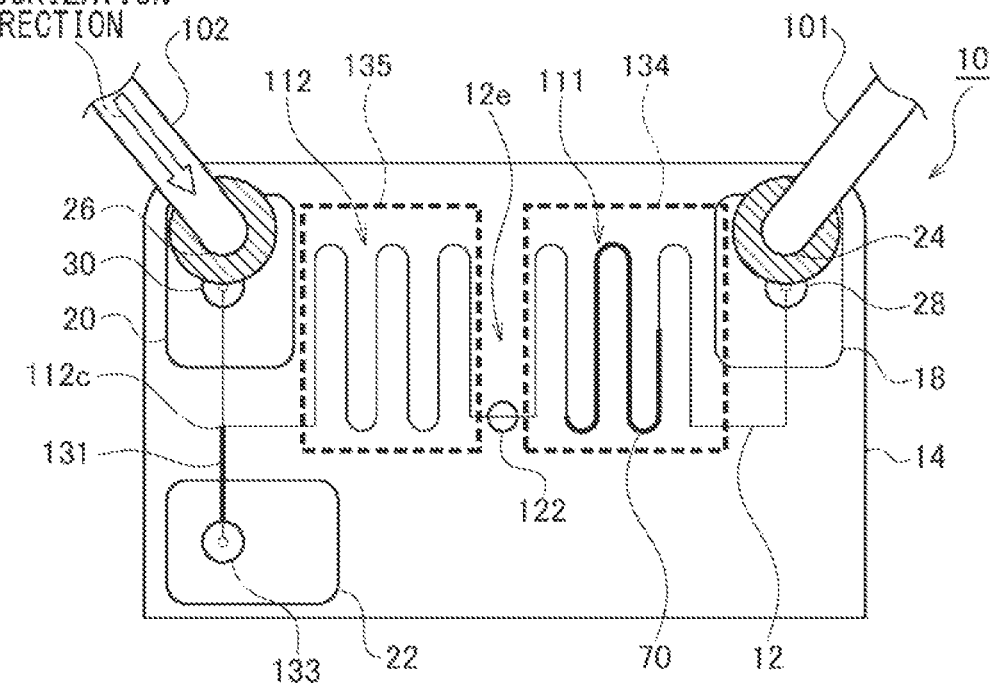
FIG. 12 is a diagram showing a condition where the pump system is operated so as to move the sample in the first embodiment.

FIG. 12 shows a condition where the pump system 110 is operated so as to move the sample 70. Either one of the first pump 103 and the second pump 104 is operated so as to move the sample 70 to the high temperature part 111 or the medium temperature part 112 of the thermal cycle region 12e. In FIG. 12, the second pump 104 to which the second nozzle 102 is connected is operated, and the first pump 103 to which the first nozzle 101 is connected is stopped. In other words, the first air communication port 24 to which the first nozzle 101 extending from the first pump 103 is connected is open to the atmospheric pressure. When the second pump 104 is operated to feed the air from the second nozzle 102 to the second air communication port 26, the sample 70 moves, passing through the medium temperature part 112 and moving to the high temperature part 111. This state is assumed to be an initial state.

More specifically, at the start of the operation of the second pump 104 or immediately before the start of the operation of the second pump 104, monitoring of the fluorescence emitted from the sample in the channel is started using the fluorescence detection optical probe 122. When there is nothing at a measurement point of the fluorescence detection optical probe 122, fluorescence that is detected is at zero or at a background level. When the sample 70 exists at the measurement point, fluorescence is detected. Therefore, monitoring of the fluorescence is started before the operation of the second pump 104 starts, the completion of the movement of the sample 70 to the high temperature part 111 is recognized through a fluorescence value rising from the background level and dropping to the background level again, and stopping the operation of the second pump 104 at this point completes the setting of the initial state. Also, when the fluorescence detection optical probe is further located in the high temperature part 111, it is also possible to stop the sample 70 at the high temperature part 111 more certainly.

It should be noted that the sample 70 located inside the branched channel 131 stays around the place even when the second pump 104 is operated. This is because the sample introduction port 133 is sealed with the third sealing film 22. The sample 70 located inside the branched channel 131 is not subjected to PCR.

After the setting to the initial state, a thermal cycle is applied to the sample 70 to progress the PCR. The measurement of fluorescence by the fluorescence detection optical probe 122 is continued.

(A) First, the sample 70 is allowed to sit for 1 to 30 seconds in the high temperature part 111 (about 94° C. atmosphere) (denaturation: thermal denaturation step). Through this step, double-stranded DNA is denatured into single strands.

(B) Next, the first pump 103 to which the first nozzle 101 is connected is operated to move the sample 70 to the medium temperature part 112 (about 60° C. atmosphere). More specifically, the sample 70 is pushed in a direction from the high temperature part 111 to the medium temperature part 112 by the action of the first pump 103. Since the fluorescence measurement by the fluorescence detection optical probe 122 continues, the operation of the first pump 103 is stopped at the point of time when a fluorescence amount rises from the background level and drops again due to the sample 70 passing through the measurement point of the fluorescence detection optical probe 122 (or after a certain period of time has passed after the fluorescence amount has decreased). Further, when the fluorescence detection optical probe 122 is located at the medium temperature part 112, it is also possible to more certainly stop the sample 70 at the medium temperature part 112.

(C) In the medium temperature part 112, the sample 70 is allowed to sit for 3 to 60 seconds (annealing+elongation: annealing step+elongation step). Through these steps, binding of primers contained in the sample 70 in advance occurs resulting in further elongated DNA.

(D) Next, the second pump 104 to which the second nozzle 102 is connected is operated to move the sample 70 from the medium temperature part 112 to the high temperature part 111. The timing for stopping the pump operation is determined based on changes in the fluorescence amount measured by the fluorescence detection optical probe 122 in the same manner as described above. After moving the sample 70 to the high temperature part 111, the sample 70 is allowed to sit for 1 to 30 seconds to go through heat denaturation.

(E) By repeating the above (B) to (D) for a predetermined number of cycles, applying a thermal cycle to the sample 70, and allowing the DNA contained in the sample 70 to undergo a plurality of cycles of thermal denaturation, annealing, and elongation steps, the amplification of DNA is performed. The number of cycles is appropriately determined by a combination of target DNA, primers, enzymes, and the like.

After the completion of a predetermined number of thermal cycles, the first pump 103 and the second pump 104 are stopped, and the PCR is ended. Even when the predetermined number of thermal cycles are applied, the fluorescence is measured by the fluorescence detection optical probe 122, and the fluorescence detected from the sample 70 increases as the DNA contained in the sample 70 is amplified. Thereby, the concentration of the sample 70 can be accurately known.

According to the PCR reaction vessel 10 according to the first embodiment, by providing the first filter 28 between the first air communication port 24 and the channel 12 and the second filter 30 between the second air communication port 26 and the channel 12, contamination inside the channel 12 can be prevented. Although the implementation of measures to prevent contamination on the side of the pump system 110 is likely to increase the cost, in the PCR reaction vessel 10 according to the first embodiment, the measures allow contamination to be prevented only on the PCR reaction vessel 10 side and are thus economical. Further, when the PCR reaction vessel is used as a disposable vessel, since the filter is always a new one, contamination can be further prevented at low cost. Furthermore, regarding the disposal of the PCR reaction vessel, since the sample is substantially sealed in the PCR reaction vessel, the disposal is also meaningful in terms of safety and environment.

In the PCR device 100 according to the first embodiment, the sample can be caused to reciprocate inside the channel 12 of the PCR reaction vessel 10 by alternately operating the first pump 103 and the second pump 104 that allow the pressures on the primary side and the secondary side to become equal when stopped. In this case, since excessive pressure is not applied to the sample during the liquid feeding (applying pressure to the sample in the channel) and, further, the pressure in the channel is not reduced, evaporation and boiling (foaming) of the liquid containing the sample due to the action of the high temperature part 111 can be prevented.

Further, in the PCR device 100 according to the first embodiment, the fluorescence from the sample is monitored all the time even during PCR in the thermal cycle region (real-time PCR). As a result, the end timing of the PCR can be determined based on the fluorescence amount that has been measured. Further, by monitoring a change in fluorescence by the fluorescence detection optical probe 122, the passing of the sample can be known, and, based on the change in the fluorescence amount accompanying the passing of the sample, the alternate operation of the first pump 103 and the second pump 104 can be controlled. Thus, the sample to be subjected to the PCR can be accurately positioned to the high temperature part 111 or the medium temperature part 112 of the thermal cycle region.

On the other hand, in the case of a PCR reaction vessel and a PCR device having a reaction region where the above-described temperatures of three levels: the high temperature part; medium temperature part; and low temperature part, are controlled, the steps, heat denaturation, annealing, and elongation, can be performed at the high temperature part, at the medium temperature part, and at the low temperature part, respectively. Also, the control thereof can be easily developed and improved by those skilled in the art based on the above detailed description. Those skilled in the art can appropriately choose, depending on the characteristics of the sample, whether the reaction region is set to have two levels or three levels.

Second Embodiment

Figure 13A:
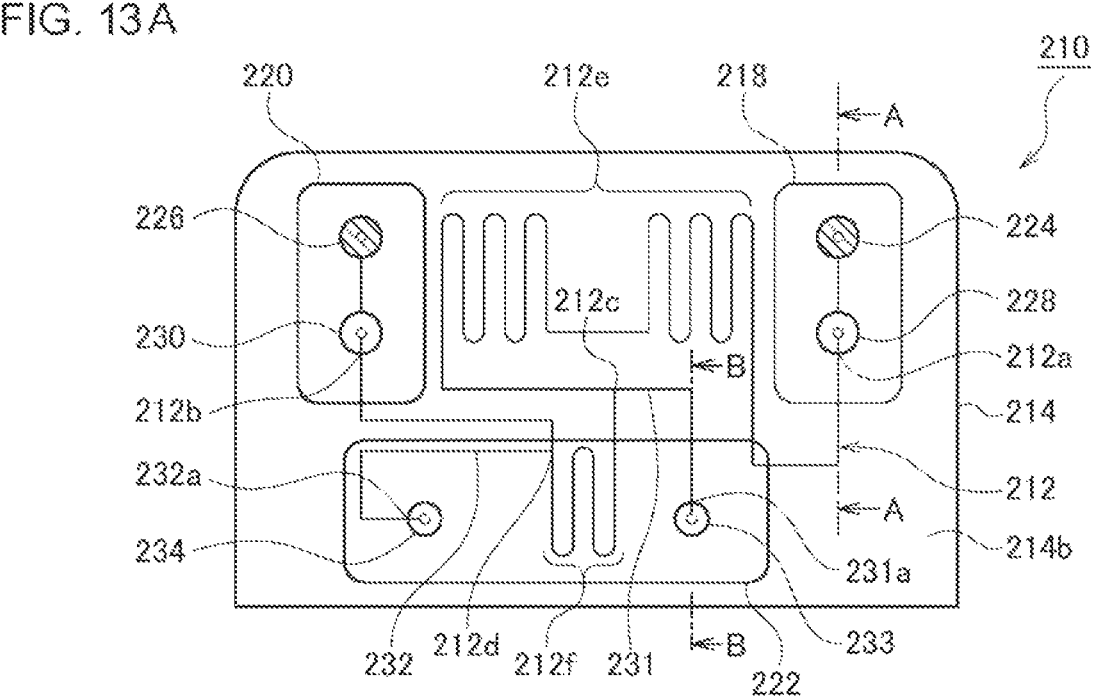
FIGS. 13A and 13B are diagrams for explaining a PCR reaction vessel according to a second embodiment of the present invention.
Figure 13B:
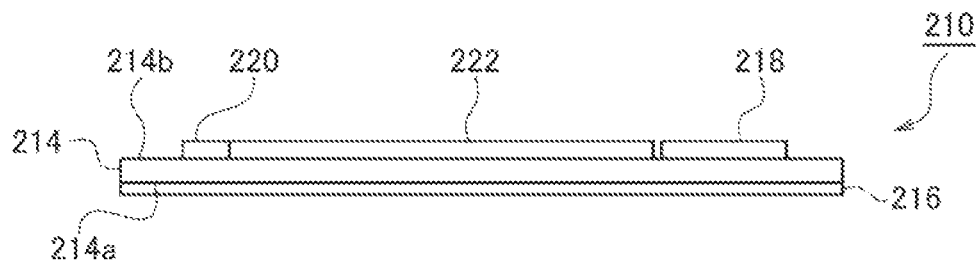
Figure 14:
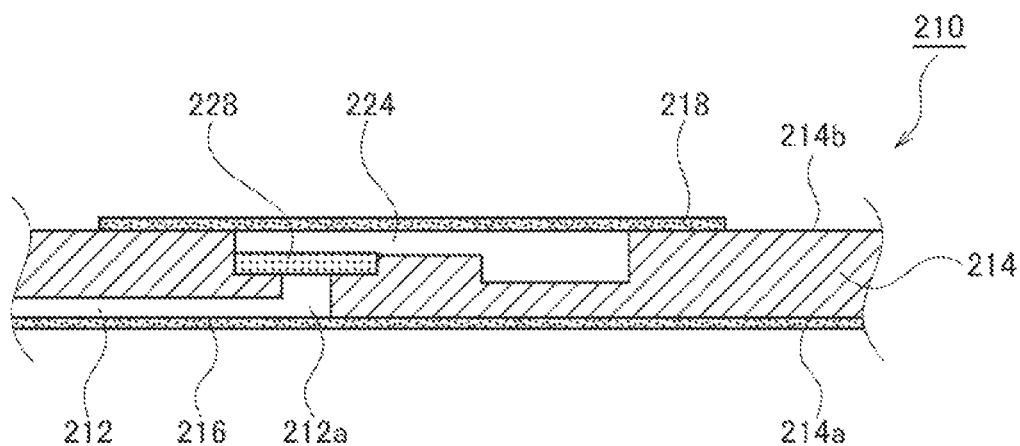
FIG. 14 is a cross-sectional view of the PCR reaction vessel shown in FIG. 13A that is sectioned along line A-A.
Figure 15:
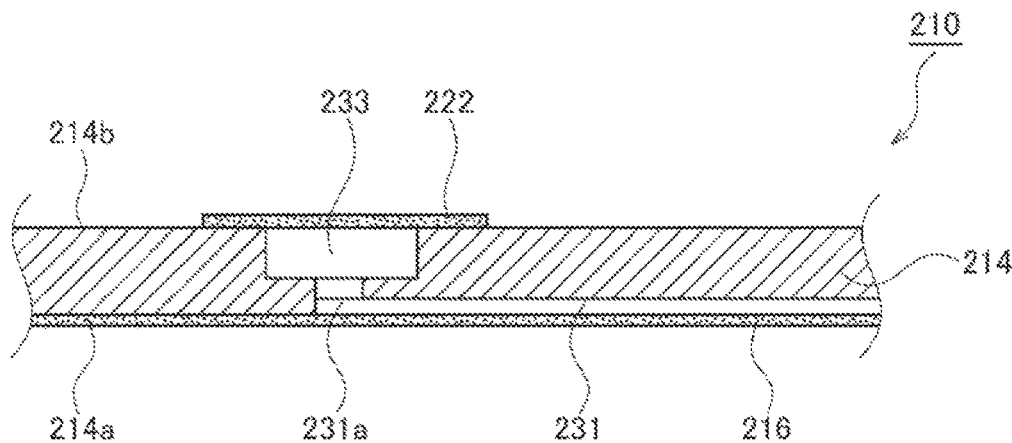
FIG. 15 is a cross-sectional view of the PCR reaction vessel shown in FIG. 13A that is sectioned along line B-B.
Figure 16:
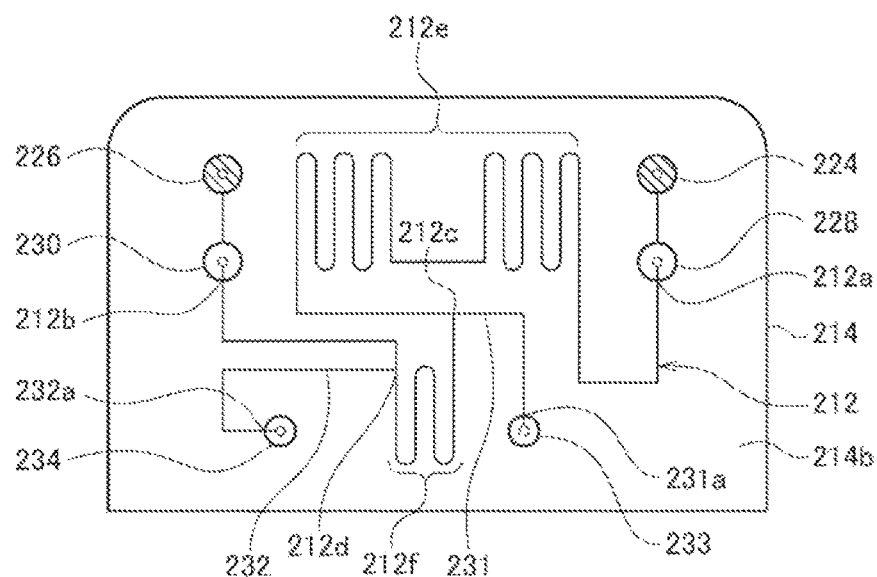
FIG. 16 is a plan view of a substrate provided in the PCR reaction vessel according to the second embodiment.
Figure 17:
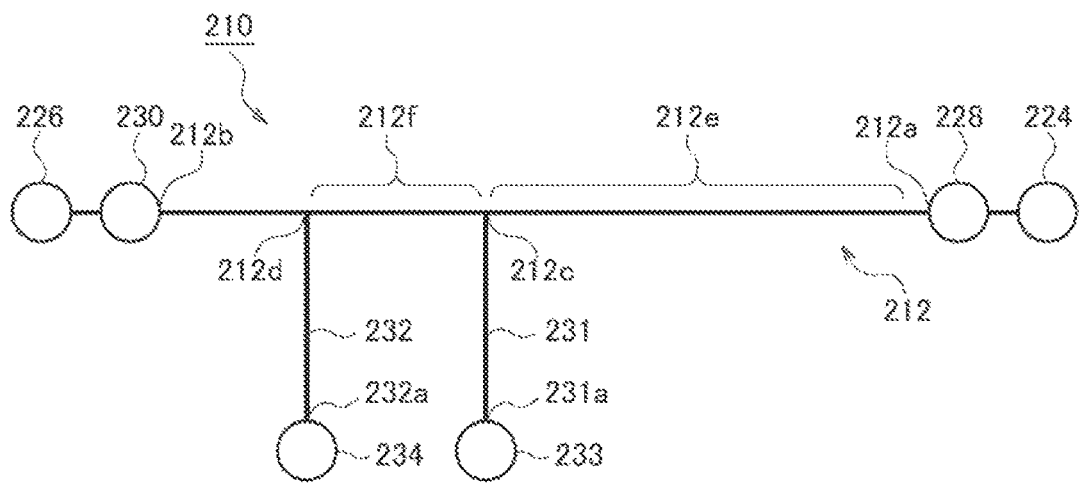
FIG. 17 is a conceptual diagram for explaining the configuration of the PCR reaction vessel according to the second embodiment.

FIGS. 13A and 13B are diagrams for explaining a PCR reaction vessel 210 according to a second embodiment of the present invention. FIG. 13A is a plan view of the PCR reaction vessel 210, and FIG. 13B is a front view of the PCR reaction vessel 210. FIG. 14 is a cross-sectional view of the PCR reaction vessel 210 shown in FIG. 13A that is sectioned along line A-A. FIG. 15 is a cross-sectional view of the PCR reaction vessel 210 shown in FIG. 13A that is sectioned along line B-B. FIG. 16 is a plan view of a substrate 214 provided in the PCR reaction vessel 210. FIG. 17 is a conceptual diagram for explaining the configuration of the PCR reaction vessel 210. The PCR reaction vessel 210 in the second embodiment is different from that in the first embodiment in that the PCR reaction vessel is provided with two branch points (a first branch point 212c and a second branch point 212d), two branched channels and two sample introduction ports extended from the branch points (a first branched channel 231 and a first sample introduction port 233, a second branched channel 232 and a second sample introduction port 234), and a buffer channel region 212f between the first branch point 212c and the second branch point 212d.

The PCR reaction vessel 210 comprises a resinous substrate 214 having a groove-like channel 212 formed on a lower surface 214a thereof, a channel sealing film 216, which is attached on the lower surface 214a of the substrate 214, for sealing the channel 212, and three sealing films (a first sealing film 218, a second sealing film 220, and a third sealing film 222) attached on an upper surface 214b of the substrate 214.

The substrate 214 is preferably formed of a material that has good thermal conductivity, is stable against temperature change, and is resistant to a sample solution that is used. Further, the substrate 214 is preferably formed of a material that has good moldability, good transparency and barrier property, and low self-fluorescence property. As such a material, an inorganic material such as glass, silicon, or the like, a resin such as acrylic, polyester, silicone, or the like, and, particularly, cycloolefin are preferred. An example of the dimensions of the substrate 214 includes a long side of 70 mm, a short side of 42 mm, and a thickness of 3 mm. An example of the dimensions of the channel 212 formed on the lower surface 214a of the substrate 214 includes a width of 0.5 mm and a depth of 0.5 mm.

As described above, the groove-like channel 212 is formed on the lower surface 214a of the substrate 214, and this channel 212 is sealed by the channel sealing film 216 (see FIG. 14). A first air communication port 224 is formed at the position of one end 212a of the channel 212 in the substrate 214. A second air communication port 226 is formed at the position of the other end 212b of the channel 212 in the substrate 214. The pair, the first air communication port 224 and the second air communication port 226, is formed so as to be exposed on the upper surface 214b of the substrate 214. Such a substrate can be produced by injection molding or cutting work with an NC processing machine or the like.

A first filter 228 is provided between the first air communication port 224 and one end 212a of the channel 212 in the substrate 214 (see FIG. 14). A second filter 230 is provided between the second air communication port 226 and the other end 212b of the channel 212 in the substrate 214. The pair, the first filter 228 and the second filter 230, provided at respective ends of the channel 212 has good low impurity characteristics and also allows only air to pass therethrough so as to prevent contamination such that the quality of DNA amplified by PCR does not deteriorate. As a filter material, polyethylene, PTFE, and the like are suitable, and the filter material may be porous or hydrophobic. Regarding the dimensions of the first filter 228 and the second filter 230, the first filter 228 and the second filter 230 are formed so as to fit without any gap in a filter installation space formed in the substrate 214.

At a first branch point 212c located between the first filter 228 and the second filter 230, a first branched channel 231 branching from the channel 212 is formed in the substrate 214. A first sample introduction port 233 is formed at the position of a terminal end 231a of the first branched channel 231 in the substrate 214 (see FIG. 15). At a second branch point 212d located between the first branch point 212c and the second filter 230, a second branched channel 232 branching from the channel 212 is further formed in the substrate 214. A second sample introduction port 234 is provided at the position of a terminal end 232a of the second branched channel 232 in the substrate 214. The first sample introduction port 233 and the second sample introduction port 234 are formed so as to be exposed on the upper surface 214b of the substrate 214.

A section of the channel 212 that is located between the first filter 228 and the first branch point 212c forms a thermal cycle region 212e intended for a high temperature region and a medium temperature region in order to apply a thermal cycle to the sample. The thermal cycle region 212e of the channel 212 includes a serpentine channel. This is for efficiently providing the amount of heat provided from the PCR device during a PCR step to a sample and for allowing the volume of a sample that can be subjected to PCR to be a certain amount or more. The thermal cycle region 212e is provided with a pair of reaction regions each including a serpentine channel and with a connection region connecting the pair of reaction regions.

A section of the channel 212 that is located between the first branch point 212c and the second branch point 212d forms the buffer channel region 212f. The buffer channel region 212f of the channel 212 includes a serpentine channel. The volume of the buffer channel region 212f of the channel 212 is set to a predetermined volume according to the amount of a sample on which a PCR process is intended to be performed. The function of the buffer channel region will be described later.

In the PCR reaction vessel 210 according to the second embodiment, most of the channel 212 is formed in the shape of a groove exposed on the lower surface 214a of the substrate 214. This is for allowing for easier molding by injection molding using a metal mold or the like. In order to make use of this groove as a channel, the channel sealing film 216 is attached on the lower surface 214a of the substrate 214. The channel sealing film 216 may be sticky on one of the main surfaces thereof or may have a functional layer that exhibits stickiness or adhesiveness by pressing that is formed on one of the main surfaces. Thus, the channel sealing film 216 has a function of being easily able to become integral with the lower surface 214a of the substrate 214 while being in close contact with the lower surface 214a. The channel sealing film 216 is desirably formed of a material, including an adhesive, that has a low self-fluorescence property. In this respect, a transparent film made of a resin such as a cycloolefin polymer, polyester, polypropylene, polyethylene or acrylic is suitable but is not limited thereto. Further, the channel sealing film 216 may be formed of a plate-like glass or resin. Since rigidity can be expected in this case, the channel sealing film 16 is useful for preventing warpage and deformation of the PCR reaction vessel 210.

Further, in the PCR reaction vessel 210 according to the second embodiment, the first air communication port 224, the second air communication port 226, the first sample introduction port 233, the second sample introduction port 234, the first filter 228, and the second filter 230 are exposed on the upper surface 214b of the substrate 214. Therefore, in order to seal the first air communication port 224 and the first filter 228, the first sealing film 218 is attached to the upper surface 214b of the substrate 214. Therefore, in order to seal the second air communication port 226 and the second filter 230, the second sealing film 220 is attached to the upper surface 214b of the substrate 214. Therefore, in order to seal the first sample introduction port 233 and the second sample introduction port 234, the third sealing film 222 is attached to the upper surface 214b of the substrate 214.

The first sealing film 218 that is used has a size that is capable of sealing the first air communication port 224 and the first filter 228 at the same time, and the second sealing film 220 that is used has a size that is capable of sealing the second air communication port 226 and the second filter 230 at the same time. A pressure-type pump (described later) is connected to the first air communication port 224 and the second air communication port 226 by perforating the first air communication port 224 and the second air communication port 226 by a hollow needle (syringe needle with a sharp tip) provided at the tip of the pump. Therefore, the first sealing film 128 and the second sealing film 220 are preferably films made of a material that is easily perforated by the needle and/or have a thickness that is easily perforated by the needle. In the second embodiment, the sealing films each having a size that is capable of sealing corresponding air communication port and filter at the same time are described. However, these air communication port and filter may be sealed separately. Alternatively, a sealing film may be used that can seal the first air communication port 224, the first filter 228, the second air communication port 226, and the second filter 230 all at once (by a single sheet).

As the third sealing film 222, a sealing film having a size that is capable of sealing the first sample introduction port 233 and the second sample introduction port 234 at the same time is used. Introduction of a sample into the channel 212 through the first sample introduction port 233 and the second sample introduction port 234 is performed by once peeling the third sealing film 222 from the substrate 214, and, after the introduction of a predetermined amount of sample, the third sealing film 222 is put back being attached to the upper surface 214b of the substrate 214 again. Therefore, as the third sealing film 222, a film is desired that is sticky enough to hold up through several cycles of attaching and peeling. Alternatively, as the third sealing film 222, a new film may be attached after the introduction of a sample. In this case, the importance of the property related to attaching and peeling can be lessened. In the second embodiment, the sealing films each having a size that is capable of sealing the first sample introduction port 233 and the second sample introduction port 234 at the same time are described. However, these air communication port and filter may be sealed separately.

In the same way as in the channel sealing film 216, the first sealing film 218, the second sealing film 220, and the third sealing film 222 may have an adhesive layer or a functional layer exhibiting stickiness or adhesiveness by pressing that is formed on one of the main surfaces thereof. The first sealing film 218, the second sealing film 220, and the third sealing film 222 are desirably formed of a material, including an adhesive, that has a low self-fluorescence property. In this respect, a transparent film made of a resin such as cycloolefin (COP), polyester, polypropylene, polyethylene or acrylic is suitable but is not limited thereto. As described above, the property such as stickiness or the like desirably do not degrade to such an extent that the use is affected even after attaching and peeling of multiple times. However, in a case where a new film is attached after the peeling and the introduction of a sample or the like, the importance of this property related to the attaching and peeling can be lessened.

An explanation will be given next regarding a method of using the PCR reaction vessel 210 configured as described above. First, a sample to be amplified through a thermal cycle is prepared. The sample includes those obtained by adding a plurality of types of primers, a thermostable enzyme and four types of deoxyribonucleoside triphosphates (dATP, dCTP, dGTP, dTTP) as PCR reagents to a mixture containing two or more types of DNA. Next, the third sealing film 222 is peeled off from the substrate 214 such that the first sample introduction port 233 and the second sample introduction port 234 are open.

Figure 18:
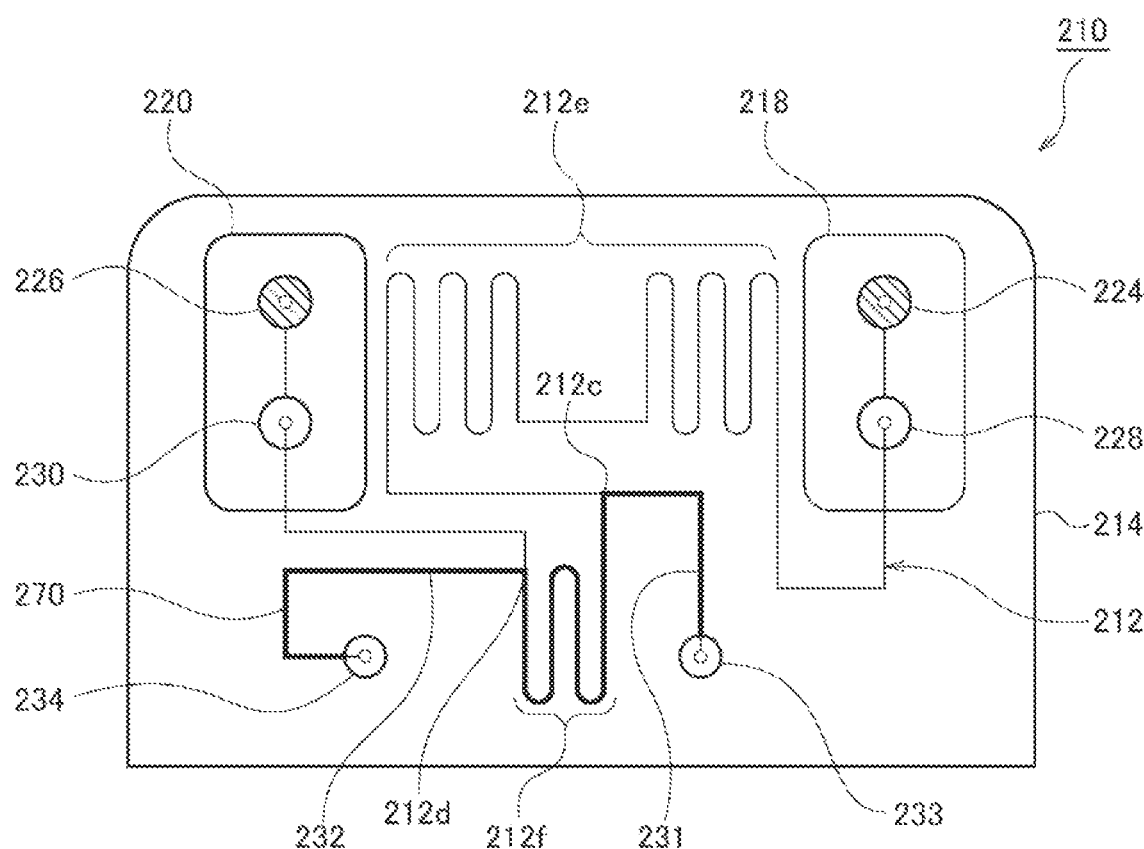
FIG. 18 is a diagram schematically showing a condition where a sample is introduced into the PCR reaction vessel in the second embodiment.

The sample is then introduced to either one of the first sample introduction port 233 and the second sample introduction port 234 by a dropper, a syringe, or the like. FIG. 18 schematically shows a condition where a sample 270 is introduced into the PCR reaction vessel 210. In FIG. 18, in order to emphasize the position of the sample 270, the sample 270 is shown by a solid line that is thicker than that for the channel 212. It should be noted that the solid line does not indicate a state where the sample 270 overflows outside the channel.

As shown in FIG. 18, the sample 270 introduced to either one of the first sample introduction port 233 and the second sample introduction port 234 fills the channel by being pushed in by a dropper, a syringe, or the like, or by a capillary phenomenon. The sample 270 is packed in the buffer channel region 212f located between the first branch point 212c and the second branch point 212d in the channel 212. However, the sample 270 does not enter the side of the thermal cycle region 212e or the second air communication port 26 of the channel 212 beyond the first branch point 212c and the second branch point 212d, which are respectively located at both ends in the buffer channel region 212f. This is because the both ends of the channel (i.e., the first air communication port 224 and the second air communication port 226) are sealed at this point such that there is no outlet for the air to escape.

Figure 19:
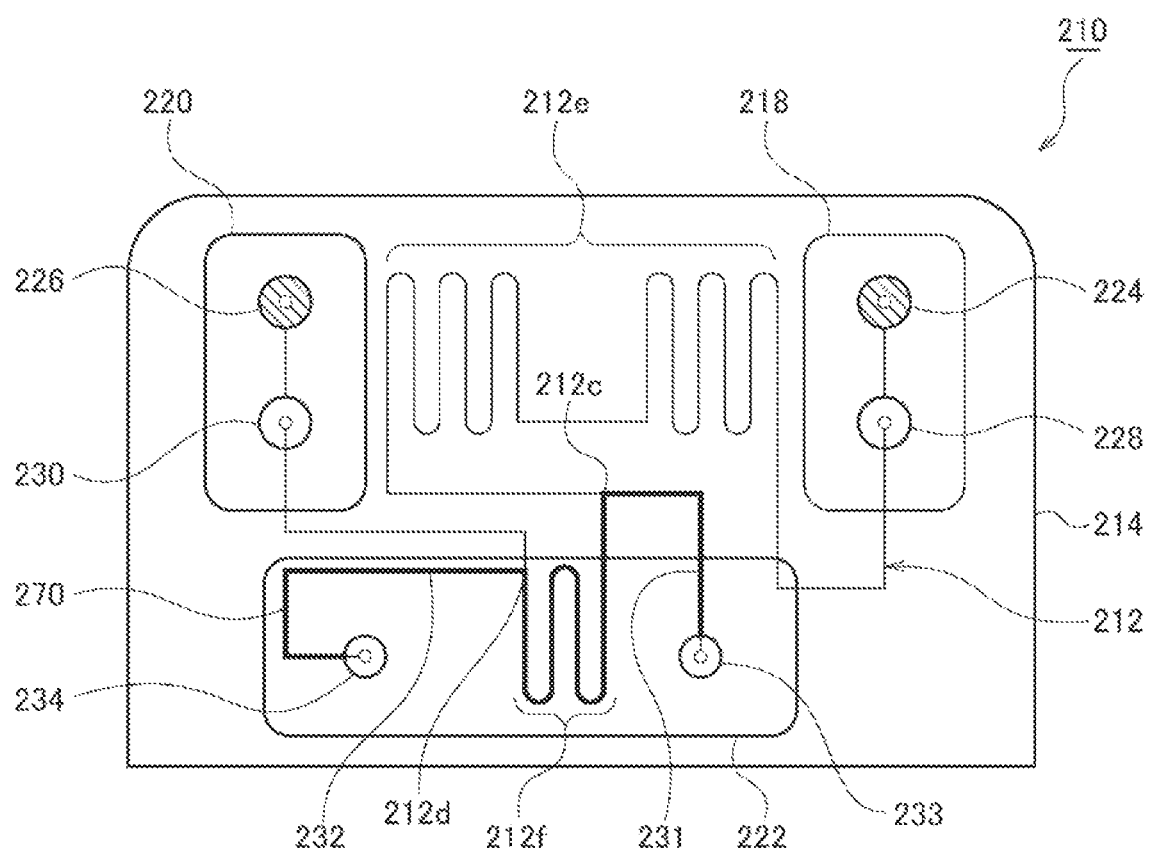
FIG. 19 is a diagram showing a state where a third sealing film is reattached to the substrate in the second embodiment.

Next, as shown in FIG. 19, the third sealing film 222 is attached back onto the substrate 214 again so as to seal the first sample introduction port 233 and the second sample introduction port 234. As described above, a new third sealing film 222 may be attached. This completes the introduction of the sample 270 into the PCR reaction vessel 210.

Figure 20:
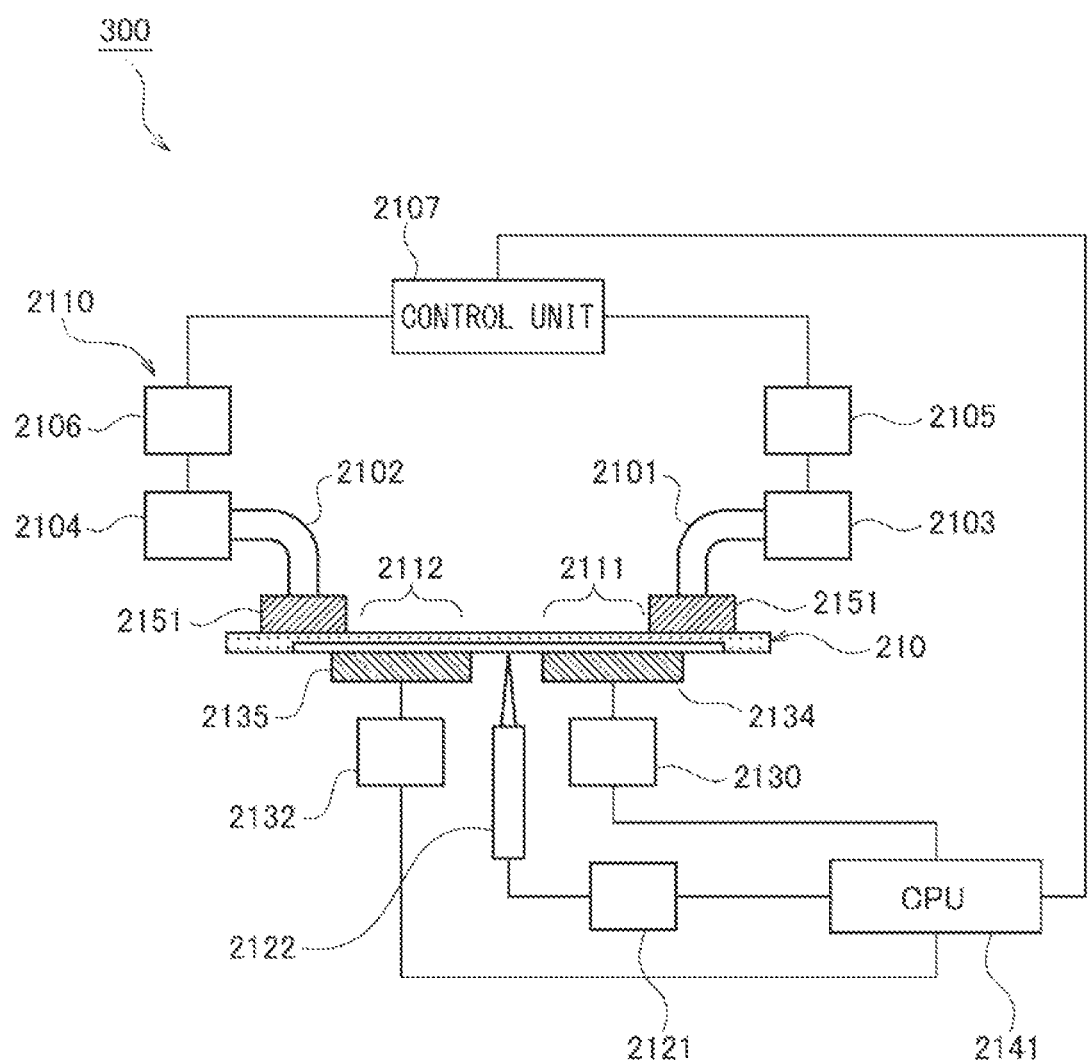
FIG. 20 is a diagram for explaining a PCR device in which the PCR reaction vessel according to the second embodiment is used.
Figure 21:
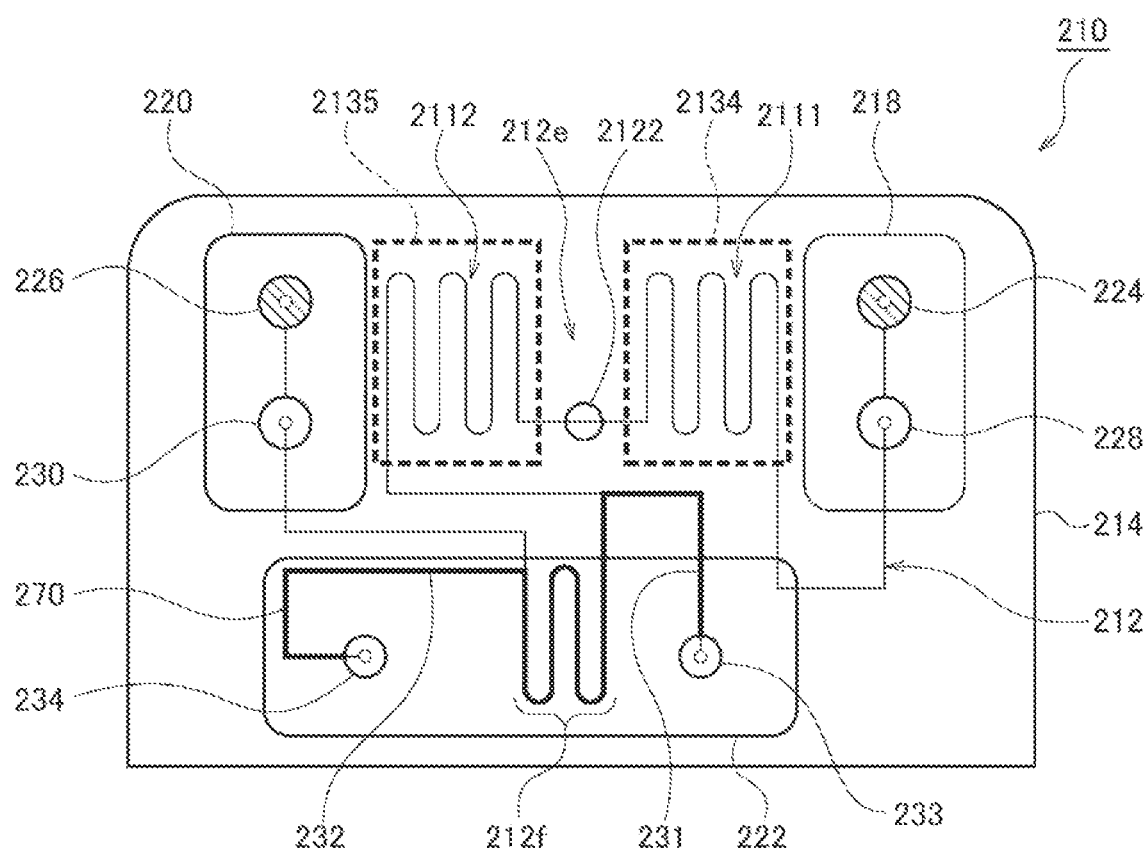
FIG. 21 is a diagram for explaining a state where the PCR reaction vessel is set at a predetermined position of the PCR device in the second embodiment.

FIG. 20 is a diagram for explaining a PCR device 300 in which the PCR reaction vessel 210 is used. FIG. 21 is a diagram for explaining a state where the PCR reaction vessel 210 is set at a predetermined position of the PCR device 300.

The PCR device 300 is provided with a fluorescence detection optical probe 2122, a first heater 2134, and a second heater 2135. As shown in FIG. 21, in the PCR reaction vessel 210, a pair of reaction regions of the thermal cycle region 212e of the channel 212 is arranged on the first heater 2134 and the second heater 2135, respectively, and the fluorescence detection optical probe 2122 is installed in the PCR device 300 so as to be located in a connection region between the pair of reaction regions. For the PCR device 300, the PCR device applied in the PCR reaction vessel according to the first embodiment can be employed.

The PCR device 300 is further provided with a pump system 2110 for causing the sample 270 to reciprocate in the thermal cycle region 212e. This pump system 2110 is provided with a first nozzle 2101, a second nozzle 2102, a first pump 2103, a second pump 2104, a first driver 2105, a second driver 2106, and a control unit 2107. The first nozzle 2101 of the pump system 2110 is connected to the first air communication port 224 of the PCR reaction vessel 210, and the second nozzle 2102 of the PCR reaction vessel 210 is connected to the second air communication port 226 of the PCR reaction vessel 210. A specific method for connecting the nozzles to the respective air communication ports will be described later. The pump system 2110 moves the sample in the thermal cycle region 212e by controlling the pressure inside the channel 212 via the first air communication port 224 and the second air communication port 226.

In the PCR device 300 according to the second embodiment, the first heater 2134 and the second heater 2135 are set to different temperatures. Each heater provides the amount of heat to individually control the temperatures of a pair of reaction regions in the thermal cycle region 212e and may be a means or a structure such as resistive heating or a Peltier element. For example, the first heater 2134 is controlled by the first heater driver 2130 so as to maintain the temperature of the reaction region on the right side of the figure page in the thermal cycle region 212e of the channel 212 to be 94° C. constantly. Also, the second heater 2135 is controlled by the second heater driver 2132 so as to maintain the temperature of the reaction region on the left side of the figure page to be 60° C. constantly. The temperature of each reaction region may be measured by a temperature sensor (not shown) such as a thermocouple, and the output to each heater may be controlled by each driver based on an electric signal therefrom. In this manner, the first heater 2134, the second heater 2135, the first heater driver 2130, the second heater driver 2132, and the temperature sensor may constitute a temperature adjustment unit for adjusting the temperature of the thermal cycle region 212e and may include other elements that improve the controllability of the temperature. This temperature adjustment unit allows the thermal cycle region 212e of the channel 212 to be divided into two region of different atmospheric temperatures. Near each heater, a temperature sensor (not shown) such as a thermocouple that measures the temperature of a corresponding part may be included, and other structures that improve the controllability of the temperature may be included. In the following, the reaction region at the atmospheric temperature of 94° C. in the channel 212 is referred to as "high temperature part 2111", and the reaction region at the atmospheric temperature of 60° C. in the channel 212 is referred to as "medium temperature part 2112". Further, in the present embodiment, a detailed explanation will be given regarding a PCR device that is provided with a PCR reaction vessel provided with a thermal cycle region where temperature ranges of two levels are set as two reaction regions and that is provided with a temperature control unit. However, the PCR device may be provided with a PCR reaction vessel provided with a thermal cycle region where temperature ranges of three or more levels can be set and that is provided with a temperature control unit. In this case, (although not shown), for example, the PCR device may be provided with a PCR reaction vessel provided with reaction regions in which a low temperature part, a medium temperature part, and a high temperature part are arranged from the left side of the figure page and with a temperature control unit. In such a case, for example, the low temperature part, the medium temperature part, and the high temperature part are controlled to maintain 50 to 70° C., at 72° C., and 94° C., respectively.

The pump system 2110 is arranged to cause the sample 270 to reciprocate within the thermal cycle region 212e of the channel 212, as described above. By alternately operating the first pump 2103 and the second pump 2104 through the first driver 2105 and the second driver 2106 under a certain condition by the control unit 2107, the sample 270 can be reciprocated between the high temperature part 2111 and the medium temperature part 112 of the channel 212, and a thermal cycle can be applied to the sample 270 under a certain condition. In the PCR device 300 according to the second embodiment, the first pump 2103 and the second pump 2104 are air pumps or blower pumps of a type where, when both the first pump 2103 and the second pump 2104 are stopped, the atmospheric pressures on a primary side and a secondary side instantaneously become equal to each other, and when both first pump 2103 and the second pump 2104 are being stopped, the atmospheric pressure on the primary side and the atmospheric pressure on the secondary side are equal to each other. If this type of pump is not used, that is, if a pump is used that maintains the immediately preceding pressure even when stopped, there is a possibility that a phenomenon occurs where the sample continues to move slightly even in the case where the pump is stopped such that the sample does not stop in a predetermined reaction region and the temperature of the sample cannot be appropriately controlled. On the other hand, external air and the channel of the PCR reaction vessel communicate with each other in terms of the atmospheric pressure when stopped (when opened), having equal atmospheric pressure; however, since a filter is provided between the air communication port and the channel, contamination into the channel can be prevented.

The sample 270 can undergo PCR by the above-described thermal cycle, and the fluorescence from the sample 270 in the channel can be detected, and the value thereof can be used as an index serving as information for determining the progress of the PCR or the termination of the reaction. As the fluorescence detection optical probe 2122 and the driver 2121, optical fiber-type fluorescence detector FLE-510 (manufactured by Nippon Sheet Glass Co., Ltd.) can be used, which is a very compact optical system that allows for rapid measurement and the detection of fluorescence regardless of a light and/or dark atmosphere. This optical fiber type fluorescence detector can be also arranged easily in a narrow space between the two temperature regions in the thermal cycle region. This optical fiber type fluorescence detector allows the wavelength characteristic of the excitation light/fluorescence to be tuned such that the wavelength characteristic is suitable for the fluorescence characteristic of the sample 270 and thus allows an optimum optical and detection system for a sample having various characteristics to be provided. Further, fluorescence detection optical probes 2122 and drivers 2121 may be provided that are installed at a plurality of sites throughout the thermal cycle region 212e. For example, the fluorescence detection optical probes 2122 and drivers 2121 may be installed to detect the fluorescence from the sample 270 in the channel located in the high temperature part 111 or the medium temperature part 2112.

In addition to the function of acquiring information for determining the progress or the termination of the PCR, the fluorescence detection optical probes 2122 and drivers 2121 can also function as position sensors for detecting, without fail, whether or not the sample 270 is in the high temperature part 2111 or the medium temperature part 2112.

In the PCR device 300 configured as described above, the control unit 2107 of the pump system 2110, the driver 2121 of the fluorescence detection optical probe 2122, the first heater driver 2130, and the second heater driver 2132 are controlled to operate optimally by a CPU 2141. Also, as described above, in the case where a reaction region in which temperatures od three levels are set, a third heater driver (not shown) is also controlled by the CPU in addition to the above.

Figure 22:
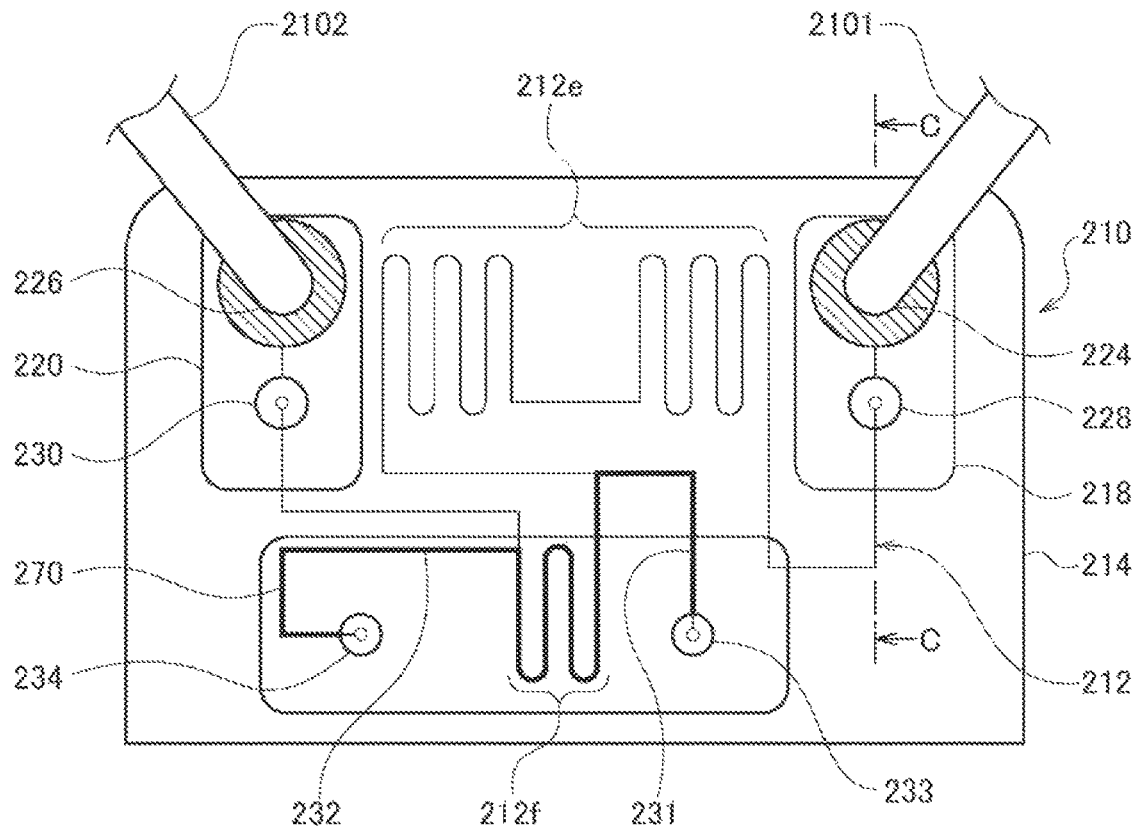
FIG. 22 is a diagram showing a condition where a nozzle of a pump system and an air communication port of the PCR reaction vessel are connected in the second embodiment.
Figure 23:
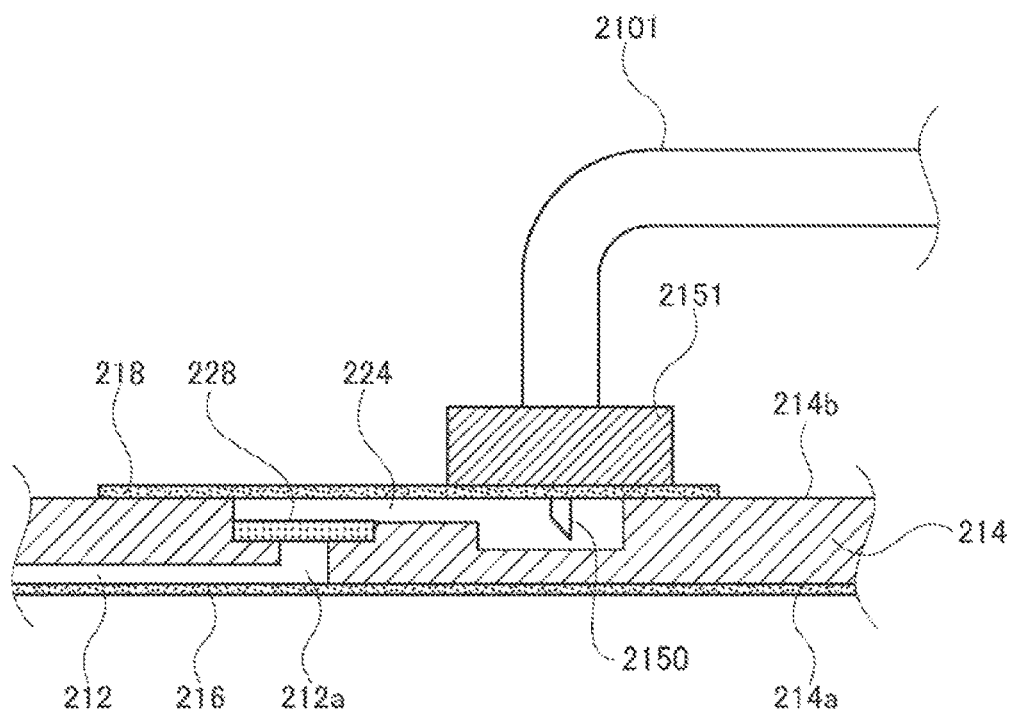
FIG. 23 is a cross-sectional view of the PCR reaction vessel shown in FIG. 22 that is sectioned along line C-C.

FIG. 22 is a diagram showing a condition where a nozzle of a pump system and an air communication port of the PCR reaction vessel are connected. FIG. 23 is a cross-sectional view of the PCR reaction vessel 210 shown in FIG. 23 that is sectioned along line C-C. As described above, the first nozzle 2101 is connected to the first air communication port 224, and the second nozzle 2102 is connected to the second air communication port 226.

As shown in FIG. 23, a needle 2150 is provided at the tip of the first nozzle 2101. By perforating the first sealing film 218 with this needle 2150, the first nozzle 2101 is connected to the first air communication port 224. The same applies to the connection between the second nozzle 2102 and the second air communication port 226.

The needle 2150 is provided with a packing material 2151 made of a soft resin that comes into close contact with the surface of a sealing film in order to secure airtightness around the connection. Immediately after the PCR reaction vessel 210 is set in the PCR device 300, the pump system 2110 is not in operation and is open to the atmospheric air, and the pressure inside the channel is thus in a state where the pressure is equal to the atmospheric pressure.

Figure 24:
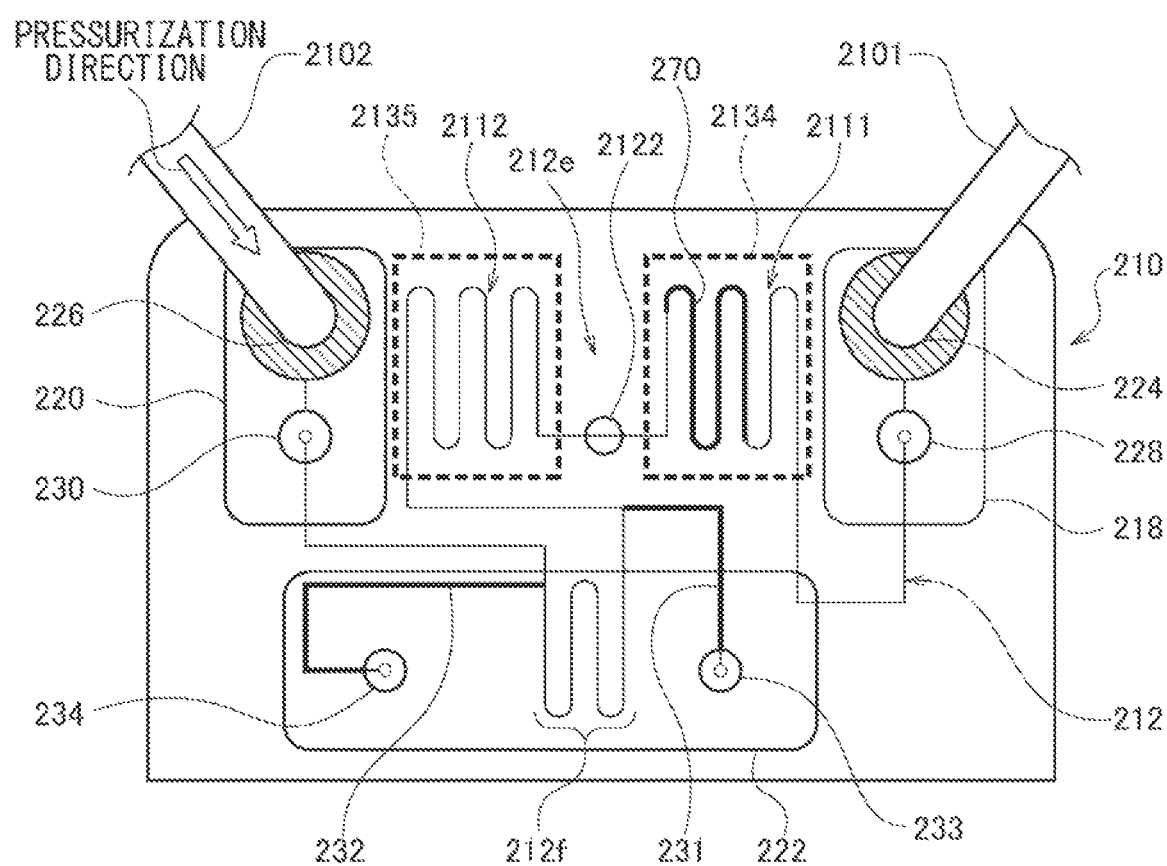
FIG. 24 is a diagram showing a condition where the pump system is operated so as to move the sample in the second embodiment.

FIG. 24 shows a condition where the pump system 2110 is operated so as to move the sample 270. Either one of the first pump 2103 and the second pump 2104 is operated so as to move the sample 270 from the buffer channel region 212f of the channel 212 to the high temperature part 2111 or the medium temperature part 2112 of the thermal cycle region 12e. In FIG. 24, the second pump 2104 to which the second nozzle 2102 is connected is operated, and the first pump 2103 to which the first nozzle 2101 is connected is stopped. In other words, the first air communication port 224 to which the first nozzle 2101 extending from the first pump 2103 is connected is open to the atmospheric pressure. When the second pump 2104 is operated to feed the air from the second nozzle 2102 to the second air communication port 226, the sample 270 moves from the buffer channel region 212f of the channel 212, passes through the medium temperature part 2112, and moves to the high temperature part 2111. This state is assumed to be an initial state.

More specifically, at the start of the operation of the second pump 2104 or immediately before the start of the operation of the second pump 2104, monitoring of the fluorescence emitted from the inside of the channel is started using the fluorescence detection optical probe 2122. When there is nothing at a measurement point of the fluorescence detection optical probe 2122, fluorescence that is detected is at zero or at a background level. When the sample 270 exists at the measurement point, fluorescence is detected. Therefore, monitoring of the fluorescence is started at the start of the operation of the second pump 2104, the completion of the movement of the sample 270 to the high temperature part 2111 is recognized through a fluorescence value rising from the background level and dropping to the background level again, and stopping the operation of the second pump 2104 at this point completes the setting of the initial state. Also, when the fluorescence detection optical probe 2122 is further located in the high temperature part 2111, it is also possible to stop the sample 270 at the high temperature part 2111 more certainly.

It should be noted that the sample 270 located inside the first branched channel 231 and the second branched channel 232 stays at the place even when the second pump 2104 is operated. This is because the first sample introduction port 233 and the second sample introduction port 234 are sealed with the third sealing film 222. The sample 270 located inside the first branched channel 231 and the second branched channel 232 is not subjected to PCR. Therefore, even when the amount of a sample that is initially introduced to the PCR reaction vessel 210 varies, by setting the volume of the buffer channel region 212f of the channel 212 formed in the PCR reaction vessel 210 to a predetermined volume according to the amount of the sample on which a PCR process is intended to be performed, a certain desired amount of sample can be always sent to the thermal cycle region 212e of the channel 212, and a fluorescence amount that affects the determination on the progress or the termination of PCR can be kept approximately constant. In other words, the buffer channel region 212f of the channel 212 has a dispensing function that allows for the extraction of a certain desired amount of sample.

After the setting to the initial state, a thermal cycle is applied to the sample 270 to progress the PCR. The measurement of fluorescence by the fluorescence detection optical probe 2122 is continued.

(A) First, the sample 270 is allowed to sit for 1 to 30 seconds in the high temperature part 2111 (about 94° C. atmosphere) (denaturation: thermal denaturation step). Through this step, double-stranded DNA is denatured into single strands.

(B) Next, the first pump 2103 to which the first nozzle 2101 is connected is operated to move the sample 270 to the medium temperature part 2112 (about 60° C. atmosphere). More specifically, the sample 270 is pushed in a direction from the high temperature part 2111 to the medium temperature part 2112 by the action of the first pump 2103. Since the fluorescence measurement by the fluorescence detection optical probe 2122 continues, the operation of the first pump 2103 is stopped at the point of time when a fluorescence amount rises from the background level and drops again due to the sample 270 passing through the measurement point of the fluorescence detection optical probe 2122 (or after a certain period of time has passed after the fluorescence amount has decreased). Further, when the fluorescence detection optical probe 2122 is located at the medium temperature part 2112, it is also possible to more certainly stop the sample 270 at the medium temperature part 2112.

(C) In the medium temperature part 2112, the sample 270 is allowed to sit for 3 to 60 seconds (annealing+elongation: annealing step+elongation step). Through these steps, binding of primers contained in the sample 270 in advance occurs resulting in further elongated DNA.

(D) Next, the second pump 2104 to which the second nozzle 2102 is connected is operated to move the sample 270 from the medium temperature part 2112 to the high temperature part 2111. The timing for stopping the pump operation is determined based on changes in the fluorescence amount measured by the fluorescence detection optical probe 2122 in the same manner as described above. After moving the sample 270 to the high temperature part 2111, the sample 270 is allowed to sit for 1 to 30 seconds to go through heat denaturation.

(E) By repeating the above (B) to (D) for a predetermined number of cycles, applying a thermal cycle to the sample 270, and allowing the DNA contained in the sample 270 to undergo a plurality of cycles of thermal denaturation, annealing, and elongation steps, the amplification of DNA is performed. The number of cycles is appropriately determined by a combination of target DNA, primers, enzymes, and the like.

After the completion of a predetermined number of thermal cycles, the first pump 2103 and the second pump 2104 are stopped, and the PCR is ended. Even when the predetermined number of thermal cycles are applied, the fluorescence is measured by the fluorescence detection optical probe 122, and the fluorescence detected from the sample 270 increases as the DNA contained in the sample 270 is amplified. Thereby, the concentration of the sample 270 can be accurately known.

According to the PCR reaction vessel 210 according to the second embodiment, by providing the first filter 228 between the first air communication port 224 and the channel 212 and the second filter 230 between the second air communication port 226 and the channel 212, contamination inside the channel 212 can be prevented. Although the implementation of measures to prevent contamination on the side of the pump system 2110 is likely to increase the cost, in the PCR reaction vessel 210 according to the second embodiment, the measures allow contamination to be prevented only on the PCR reaction vessel 210 side and are thus economical. Further, when the PCR reaction vessel is used as a disposable vessel, since the filter is always a new one, contamination can be further prevented at low cost. Furthermore, regarding the disposal of the PCR reaction vessel, since the sample is substantially sealed in the PCR reaction vessel, the disposal is also meaningful in terms of safety and environment.

Further, according to the PCR reaction vessel 210 according to the second embodiment, by providing the buffer channel region in the channel 212, a sample subjected to PCR can be dispensed, and only a required amount of sample can be always sent to the thermal cycle region of the channel 212.

In the PCR device 300 according to the second embodiment, the sample can be caused to reciprocate inside the channel 212 of the PCR reaction vessel 210 by alternately operating the first pump 2103 and the second pump 2104 that allow the pressures on the primary side and the secondary side to become equal when stopped. In this case, since excessive pressure is not applied to the sample during the liquid feeding (applying pressure to the sample in the channel) and, further, the pressure in the channel is not reduced, evaporation and boiling (foaming) of the liquid containing the sample due to the action of the high temperature part 2111 can be prevented.

Further, in the PCR device 300 according to the second embodiment, the fluorescence from the sample is monitored all the time even during PCR in the thermal cycle region (real-time PCR). As a result, the end timing of the PCR can be determined based on the fluorescence amount that has been measured. Further, by monitoring a change in fluorescence by the fluorescence detection optical probe 2122, the passing of the sample can be known, and, based on the change in the fluorescence amount accompanying the passing of the sample, the alternate operation of the first pump 2103 and the second pump 2104 can be controlled. Thus, the sample to be subjected to the PCR can be accurately positioned to the high temperature part 2111 or the medium temperature part 2112 of the thermal cycle region.

On the other hand, in the case of a PCR reaction vessel and a PCR device having a reaction region where the above-described temperatures of three levels: the high temperature part; the medium temperature part; and the low temperature part, are controlled, the steps, heat denaturation, annealing, and elongation, can be performed at the high temperature part, at the medium temperature part, and at the low temperature part, respectively. Also, the control thereof can be easily developed and improved by those skilled in the art based on the above detailed description. Those skilled in the art can appropriately choose, based on the characteristics of the sample, whether the reaction region is set to have two levels or three levels.

Described above is an explanation of the present invention based on the embodiments. These embodiments are intended to be illustrative only, and it will be obvious to those skilled in the art that various modifications to constituting elements and processes could be developed and that such modifications are also within the scope of the present invention.

In the above-stated embodiments, a pair of pumps that allows pressures on a primary side and a secondary side to be equal when stopped is arranged at the respective ends of a channel. Alternatively, a pump capable of pressurization and suctioning may be provided only at either one of the ends of the channel, and the other end may be open to the atmospheric pressure. In other words, a sample is moved in a thermal cycle region by controlling the pressure inside a channel via a first air communication port and a second air communication port. In this case, a process of switching the operations of a pair of pumps at a fixed timing is not necessary, and pump controlling is thus facilitated.

Also, in the above-described embodiments, a measurement point of a fluorescence detection optical probe is arranged between a high temperature part and a medium temperature part. Alternatively, a measurement point of a fluorescence detection optical probe may be arranged at each of the high temperature part and the medium temperature part. In this case, the accuracy for positioning a sample can be increased.

What is claimed is:

1. A PCR reaction vessel comprising:
   a substrate;
   a channel formed on the substrate;
   a pair of filters that is provided at respective ends of the channel and that is for preventing contamination inside the channel;
   a pair of air communication ports that communicate with the channel through the respective filters;
   a sample introduction port for introducing a sample that is subjected to PCR inside the channel; and
   a thermal cycle region that is formed between the pair of filters in the channel and that includes a plurality of different temperature regions capable of causing PCR in the sample;
   wherein the sample repeatedly moves in a reciprocating manner between the plurality of temperature regions,
   wherein the substrate is a parallel plate-shaped substrate and has a first surface and a second surface that faces the first surface,
   wherein the channel is formed on the first surface of the substrate,
   wherein the air communication ports are formed on the second surface of the substrate,
   wherein the thickness of the filters is smaller than the thickness of the substrate,
   wherein the filters fit in a filter installation space formed at an intermediate position between the first surface and the second surface in the substrate, and
   wherein air sent to the air communication ports passes through the filters from the second surface, reaches the first surface, and is introduced into the channel.

2. The PCR reaction vessel according to claim 1, wherein the plurality of temperature regions each include a serpentine channel.

3. The PCR reaction vessel according to claim 1, further comprising:
   a sealing film for sealing the air communication ports, the filters, and the sample introduction port; and
   a channel sealing film for sealing at least the plurality of temperature regions in the channel.

4. The PCR reaction vessel according to claim 1, wherein the thermal cycle region includes a high temperature part for causing heat denaturation in the sample and a medium temperature part for causing annealing and elongation.

5. The PCR reaction vessel according to claim 4, wherein the distance between the sample introduction port and the medium temperature part is smaller than the distance between the sample introduction port and the high temperature part.

6. A PCR device comprising:
   the PCR reaction vessel according to claim 1;
   a temperature adjustment unit for adjusting the temperature of the thermal cycle region; and
   a pump system that is connected to the air communication ports and controls the pressure inside the channel in order to move the sample inside the thermal cycle region.

7. The PCR device according to claim 6,
   wherein the pump system is provided with a pair of pumps respectively connected to the pair of air communication ports,
   wherein pressure on the primary side and pressure on the secondary side become equal in the pumps when the pumps are stopped, and
   wherein, by alternately operating the pair of pumps, the sample is caused to repeatedly move in a reciprocating manner between the plurality of temperature regions.

8. The PCR device according to claim 6,
   wherein the pump system is provided with a hollow needle, and
   wherein perforation of the sealing film for sealing the air communication ports with the needle causes the pump system and the channel to communicate with each other.

9. The PCR device according to claim 6, further comprising a fluorescence detector for detecting fluorescence generated from the sample inside the channel.

10. The PCR device according to claim 9,
    wherein the thermal cycle region is provided with a connection region connecting the plurality of temperature regions, and
    wherein the fluorescence detector detects fluorescence from the connection region.

11. The PCR device according to claim 9, further comprising a control unit for controlling the pump system based on a value detected by the fluorescence detector,
    wherein the control unit determines the progress of PCR based on the value detected by the fluorescence detector.

12. A PCR method comprising:
preparing a PCR reaction vessel including:
a parallel plate-shaped substrate;
a channel formed on the substrate;
a pair of filters that fit in installation spaces formed at respective ends of the channel and whose thickness is smaller than the thickness of the substrate;
a pair of air communication ports that communicate with the channel through the respective filters;
a sample introduction port for introducing a sample that is subjected to PCR inside the channel; and
a thermal cycle region that is formed between the pair of filters in the channel and that includes a plurality of different temperature regions capable of causing PCR in the sample;
controlling the respective temperatures of the plurality of temperature regions in the thermal cycle region such that PCR of the sample is possible;
connecting a pump system for controlling the pressure inside the channel to the air communication ports; and
controlling the pressure applied to the sample inside the channel and repeatedly moving the sample in a reciprocating manner between the plurality of temperature regions in the thermal cycle region by operating the pump system so as to cause PCR in the sample,
wherein the substrate has a first surface and a second surface that faces the first surface,
wherein the channel is formed on the first surface of the substrate,
wherein the air communication ports are formed on the second surface of the substrate;
wherein the installation spaces are formed at an intermediate position between the first surface and the second surface in the substrate, and
wherein air sent to the air communication ports passes through the filters from the second surface, reaches the first surface, and is introduced into the channel.

13. The PCR method according to claim 12, wherein the thermal cycle region includes a high temperature part for causing heat denaturation in the sample and a medium temperature part for causing annealing and elongation.

14. The PCR method according to claim 12, wherein the thermal cycle region includes a high temperature part for causing heat denaturation in the sample, a medium temperature part for causing annealing, and a low temperature part for causing elongation.

15. The PCR method according to claim 12,
wherein the PCR reaction vessel further includes:
a sealing film for sealing the air communication ports, the filters, and the sample introduction port; and
a channel sealing film for sealing at least the plurality of temperature regions in the channel.

16. The PCR method according to claim 12,
wherein the pump system is provided with a hollow needle, further comprising:
perforating the sealing film for sealing the air communication ports with the needle so as to cause the pump system and the channel to communicate with each other.

17. The PCR method according to claim 12,
wherein the thermal cycle region is provided with a connection region connecting the plurality of temperature regions, further comprising:
detecting fluorescence generated from the sample inside the connection region; and
monitoring the detected fluorescence.

18. The PCR method according to claim 17, further comprising controlling the pump system based on a change in the detected fluorescence.

\* \* \* \* \*